US010610648B2

(12) United States Patent
Cowe

(10) Patent No.: US 10,610,648 B2
(45) Date of Patent: Apr. 7, 2020

(54) MEDICAMENT DELIVERY DEVICE

(71) Applicant: Owen Mumford Limited, Woodstock, Oxfordshire (GB)

(72) Inventor: Toby Cowe, Woodstock (GB)

(73) Assignee: OWEN MUMFORD LIMITED, Woodstock, Oxfordshire (GB)

( * ) Notice: Subject to any disclaimer, the term of this patent is extended or adjusted under 35 U.S.C. 154(b) by 260 days.

(21) Appl. No.: 15/546,350

(22) PCT Filed: Jan. 27, 2016

(86) PCT No.: PCT/GB2016/000019
§ 371 (c)(1),
(2) Date: Jul. 26, 2017

(87) PCT Pub. No.: WO2016/120587
PCT Pub. Date: Aug. 4, 2016

(65) Prior Publication Data
US 2017/0361022 A1 Dec. 21, 2017

(30) Foreign Application Priority Data
Jan. 29, 2015 (GB) .................................. 1501475.6

(51) Int. Cl.
*A61M 5/315* (2006.01)
*A61M 5/20* (2006.01)
(Continued)

(52) U.S. Cl.
CPC ........ *A61M 5/3157* (2013.01); *A61M 5/2033* (2013.01); *A61M 5/28* (2013.01);
(Continued)

(58) Field of Classification Search
CPC .... A61M 5/2033; A61M 5/20; A61M 5/3202; A61M 5/24; A61M 5/3204; A61M 5/326;
(Continued)

(56) References Cited

U.S. PATENT DOCUMENTS

| 2013/0317479 A1 | 11/2013 | Brereton et al. |
| 2015/0119812 A1 | 4/2015 | Fabien et al. |
| 2015/0209505 A1* | 7/2015 | Hanson ............... A61M 5/1454 604/135 |

FOREIGN PATENT DOCUMENTS

| GB | 2488578 A | 9/2012 |
| WO | 2010/035059 A1 | 4/2010 |

(Continued)

OTHER PUBLICATIONS

International Search Report, PCT Application No. PCT/GB2016/000019, dated Apr. 18, 2016.
(Continued)

*Primary Examiner* — Manuel A Mendez
(74) *Attorney, Agent, or Firm* — Kilpatrick Townsend & Stockton LLP

(57) ABSTRACT

A device (1) for delivering an injectable drug to a patient for example from a conventional syringe (37) with a hypodermic needle. The device (1) provides to a user an audible, visible and/or tactile end of dose indication after all of the medicament has been delivered. The end of dose indication can be provided by releasing energy stored within an energy storage means (3*d*), energy having been imparted to the energy storage means (39) during the delivery of the injectable drug. The energy storage means (3*d*) acts upon an end of dose indicator (41) which interacts with another part of the device (1), for example an external housing (3), to produce the end of dose indication.

13 Claims, 15 Drawing Sheets

(51) Int. Cl.
*A61M 5/31* (2006.01)
*A61M 5/28* (2006.01)

(52) U.S. Cl.
CPC ........ *A61M 5/3146* (2013.01); *A61M 5/3158* (2013.01); *A61M 2005/206* (2013.01); *A61M 2205/581* (2013.01); *A61M 2205/582* (2013.01)

(58) Field of Classification Search
CPC .. A61M 5/3157; A61M 5/30; A61M 5/31551; A61M 5/31553
See application file for complete search history.

(56) References Cited

FOREIGN PATENT DOCUMENTS

| WO | 2013/175144 A1 | 11/2013 |
| WO | 2014/166887 A1 | 10/2014 |

OTHER PUBLICATIONS

Written Opinion, PCT Application No. PCT/GB2016/000019, dated Apr. 18, 2016.

* cited by examiner

MEDICAMENT DELIVERY DEVICE

This application is a national stage application of PCT/GB2016/000019, filed on Jan. 27, 2016, which claims priority to British Patent Application No. 1501475.6, filed on Jan. 29, 2015, both of which are incorporated herein by reference in their entireties.

The present invention relates to a medicament delivery device with an end of dose indicator. The medicament delivery device may be a single dose auto-injector for delivery of a medicament from a syringe or a multiple dose pen type injection device which delivers a medicament that is contained within a cartridge. However, the end of dose indicator is suitable for application to many types of medicament delivery devices.

A medicament delivery device having an end of dose indication, such as an audible noise, a vibration and/or tactile feedback, is desirable because the receipt of an end of dose indication informs the user of that device that all of the medicament has been delivered to them. Upon receiving the end of dose indication the user can withdraw the device from the injection site with full confidence that the injection phase has been completed. It is important that the end of dose indication is given at the correct time, i.e. not substantially before or after all of the medicament has been delivered, in order to ensure that all of the medicament has been delivered and to ensure that the time taken to undertake the injection can be kept to a minimum. The end of dose indication may be given when the bung reaches the end of the syringe barrel, or when the bung is a short distance away from the end of the barrel. The latter arrangement may be required to avoid a situation in which the bung reaches the end of its travel, i.e. it contacts the end of the barrel, before the end of dose indication is instigated.

In the field of medicament delivery devices there have been a number of proposals for end of dose indicators in auto-injectors, i.e. devices which deliver a medicament from a syringe that is placed within the device in a complete form, i.e. a syringe with a needle, barrel, bung and plunger. In those devices a driving component acts upon the plunger to move it and the bung along the barrel and thus deliver medicament through the needle. The end of dose indication is typically triggered by a mechanical interaction between a feature on the driving component and a feature on a stationary part of the device, such as the housing. One disadvantage of such prior art technology is that it is difficult to indicate the end of dose with the desired degree of accuracy. For example, in one scenario the end of dose indication should be given when the bung has travelled to the end of the barrel, i.e. when the plunger and the driving component have moved to the end of their travel and all of the medicament has been delivered. The length of that travel is determined by the length of the barrel, the bung, the plunger and the driving component and the position of the triggering feature on the stationary component of the device. Those lengths change within the allowable manufacturing tolerances of the individual components. The stack-up of those tolerances can significantly change the actual distance by which the plunger must travel to deliver the complete dose of medicament. Thus, the end of dose indication might be provided too early, i.e. at a point when the full dose of the medicament has not been administered, or too late, i.e. at a point some time after the full dose has been administered. It may also be the case that an end of dose indication is not provided at all because if the bung reaches the end of the syringe barrel then further travel of the components can be halted before the mechanical interaction occurs between the moving part and the triggering feature.

Accordingly, the present invention provides a medicament delivery device with means to provide a user with an end of dose indication, the medicament delivery device comprising a container for a medicament, a plunger for acting upon the medicament within the container to expel the medicament from the container, a plunger drive mechanism, a plunger drive energy source, a connector, an end of dose indicator and an end of dose indication energy storage means connected to the plunger by the connector by means of a releasable attachment, wherein, the device is configured such that, during its operation, movement of the plunger under the action of the drive mechanism causes energy from the drive energy source to be imparted to the indication energy storage means and to be stored by it and wherein upon the plunger reaching substantially the end of its travel the releasable attachment between the connector and the indication energy storage means is released and the indication energy storage means acts upon the end of dose indicator, the end of dose indicator interacting with the medicament delivery device to produce an end of dose indication. The invention provides an advantage because activation of the end of dose indication is directly related to the movement of the plunger and thus the variation in the timing of the end of dose indication is minimised. Furthermore, there is no need to provide a dedicated energy source for the end of dose indication because of the energy transfer from the plunger drive energy source, e.g. the plunger drive spring.

Preferably, the connector comprises a connection element and a retraction means for retracting the connection element to an un-extended position, wherein the retraction means keeps the connection element in tension during a medicament delivery phase of the operation of the device. This is advantageous because it prevents the connector from becoming tangled with other components of the device, which might hinder operation of the device.

Preferably, the connector comprises a tape and at least part of the tape is in the form of a spirally wound spring. The tape may be made from a metal, such as a spring steel, or from any other suitable material. Alternatively, the connector may be a cord or a filament which can be configured so that it restores itself to a retracted position when released.

Preferably, at least a part of the end of dose indication energy storage means is resiliently deformable and is deformed during a medicament delivery phase of the operation of the device. Alternatively, the end of dose indication energy storage means might store energy in a different form, for example as electrical energy for powering a light source.

Preferably, the releasable attachment comprises a peg attached to a striker part of the end of dose indication storage energy means. Other appropriate attachment means are envisaged.

Preferably the end of dose indication energy storage means comprises at least one resiliently deformable arm which is fixedly attached to another part of the device at a fixed end and which has a free end which is free to move, wherein the free end is provided with a striker part, the connector being attached to the arm, at least initially, wherein, during one phase of operation of the device, movement of the plunger causes the arm to deflect and during another phase of operation of the device, the connector becomes detached from the arm and the arm rebounds and strikes a part of the device, in order to produce an end of dose indication.

Preferably, the end of dose indication energy storage means comprises two resiliently deformable arms each provided with a striker part in the form of a striking head, wherein the striking heads are configured to strike the inside of a housing part of the device.

In another embodiment of the present invention, the end of dose indication energy storage means preferably comprises at least one resiliently deformable element which is fixedly attached to another part of the device at a fixed end and at its other end is fixedly attached to a striker carrier carrying at least one striker, the connector being attached to the striker carrier, at least initially, wherein, during one phase of operation of the device, movement of the plunger causes the striker carrier to rotate in a first direction and during another phase of the operation of the device, the connector becomes detached from the striker carrier and the striker carrier rotates in a second direction, driven by a rebounding of the at least one resiliently deformable element, wherein the at least one striker strikes a part of the device, in order to produce an end of dose indication.

Preferably, rotation of the striker carrier in the first direction causes the at least one striker to strike a part of the device, in order to produce an indication that a dose is being delivered whilst the plunger is moving.

Preferably, the end of dose indication energy storage means comprises at least one resiliently deformable arm which is fixedly attached to another part of the device at a fixed end and which has a free end which is free to move, wherein the free end is provided with a striker part, the connector being attached to the arm, at least initially, wherein, during one phase of operation of the device, movement of the plunger causes the arm to deflect and during another phase of operation of the device, the connector becomes detached from the arm and the arm rebounds and strikes a firing button, in order to produce an end of dose indication.

Preferably, the end of dose indication energy storage means comprises at least one resiliently deformable arm which is fixedly attached to another part of the device at a fixed end and which has a free end which is free to move, wherein the free end is provided with a striker part, the connector being attached to the arm, at least initially, wherein the device further comprises a moveable indicator and a housing part, or a firing button, with means to enable at least a part of the moveable indicator to become proud of the external surface of the device and wherein, during one phase of operation of the device, movement of the plunger causes the arm to deflect and during another phase of operation of the device, the connector becomes detached from the arm and the arm rebounds and strikes the moveable indicator and moves the moveable indicator relative to the housing part or firing button such that at least a part of the moveable indicator is at least momentarily proud of the external surface of the device. The moveable indicator may extend through a hole provided in the housing or firing button, or it may push against a membrane provided in, or on, the housing or firing button, that membrane then becoming raised above the outer surface of the device. A number of different mechanisms are suitable and envisaged here.

Figure 1:
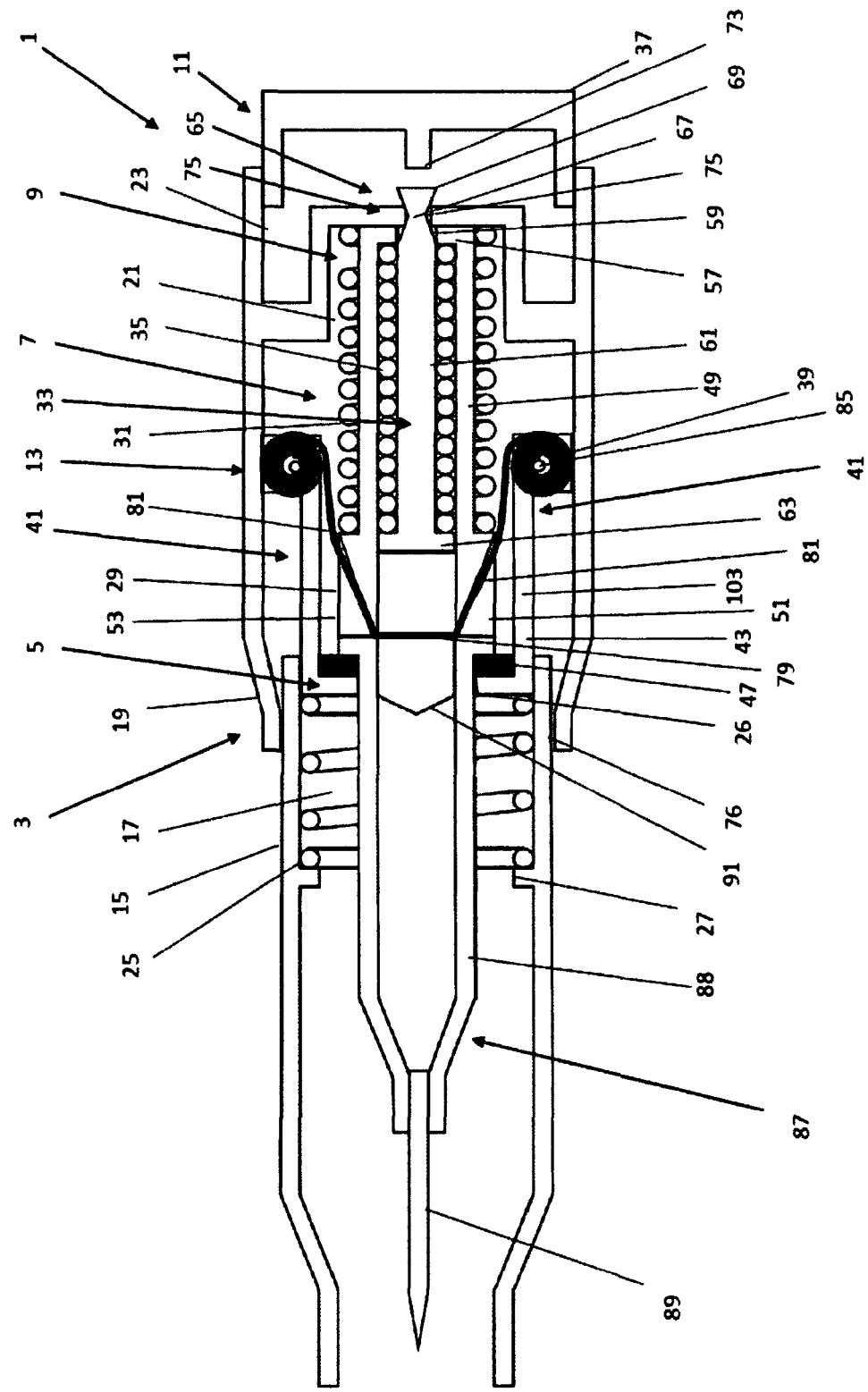
FIG. 1 is a cross-sectional view of an auto-injector according to a first embodiment of the invention, in a primed and latched position.

An auto-injector 1, according to a first embodiment of the present invention, is illustrated in FIGS. 1 to 6. The proximal end of the auto-injector 1 is the part nearest to the injection site, when the auto-injector 1 is in use. The distal end of the auto-injector 1 is the part furthest from that injection site. The auto-injector 1 comprises a housing 3 within which are located a syringe carrier 5, a needle insertion mechanism 7, a medicament delivery mechanism 9, an actuator 11 and an end of dose indication mechanism 13.

The housing 3 comprises two parts. The first part is a syringe housing 15, which is hollow and cylindrical and forms a syringe carrier chamber 17. The second is a drive mechanism housing 19.

The drive mechanism housing 19 is also hollow and cylindrical and forms a drive spring chamber 21 and an actuation mechanism recess 23. The drive spring chamber 21 is split into two halves by a slot which runs diametrically across the distal end of the drive mechanism housing 19 and extends in a longitudinal direction through the walls of the drive mechanism housing 19 that form the spring chamber 21. The drive mechanism housing 19 is provided at its distal end with a female latch part 75 in the form of a circular orifice through which the slot extends. The two parts, i.e. the syringe housing 15 and the drive mechanism housing 19, are connected together by a suitable fixing, for example an arrangement of complementary helical screw threads 76.

The syringe carrier 5 is located partially within the syringe carrier chamber 17 and partially within the drive mechanism housing 19. It is slideably engaged with the syringe housing 15 and guided by the internal walls of the syringe housing 15. The degree of travel of the syringe carrier 5 in the proximal direction within the syringe housing 15 is limited by a syringe carrier bias helical compression spring 25 located between the proximal face of a flange 26 on the syringe carrier 5 and an annular syringe carrier abutment 27 provided around the internal wall of the syringe carrier chamber 17. The syringe carrier bias helical compression spring 25 biases the syringe carrier 5 in a distal direction. The degree of travel of the syringe carrier 5 in the distal direction is limited by the abutment of the distal face of the flange 26 with the needle insertion mechanism 7 and the abutment of the needle insertion mechanism 7 with the distal end of the drive mechanism housing 19.

Located within the drive mechanism housing 19 are the needle insertion mechanism 7 and the medicament delivery mechanism 9. The needle insertion mechanism 7 comprises a syringe restraining member 29, acted upon by a syringe restraining helical compression spring 31. The syringe restraining member 29 and the syringe restraining spring 31 are located within the spring chamber 21. The medicament delivery mechanism 9 comprises an elongate plunger 33 acted upon by a plunger driving helical compression spring 35.

Also located within the drive mechanism housing 19 are the actuator 11 and the end of dose indication mechanism 13. The actuator 11 comprises an actuation button 37 with a de-latching arrangement, which in use releases the needle insertion mechanism 7 and the medicament delivery mechanism 9 from a primed and latched position. The end of dose indication mechanism 13 comprises a spirally coiled spring 39 which, when unwound as a result of operation of the medicament delivery mechanism 9, causes the deflection and subsequent rebound of strikers 41 which are provided on the syringe carrier 5 and which act upon the internal surface of the drive mechanism housing 19.

Figure 2:
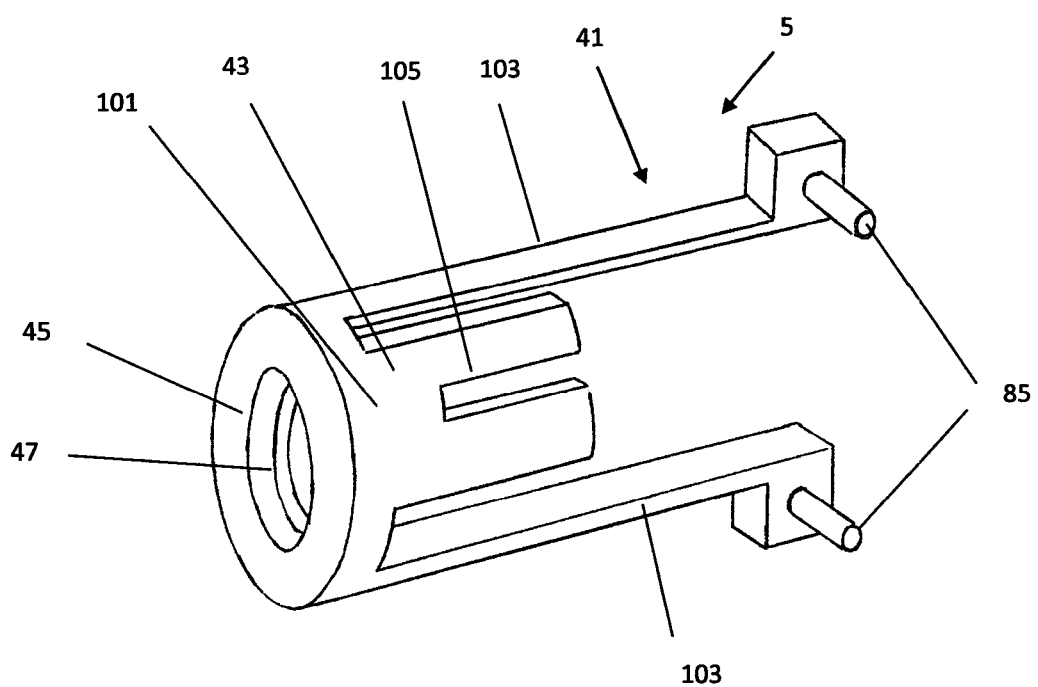
FIG. 2 is a perspective view of the syringe carrier.
Figure 3:
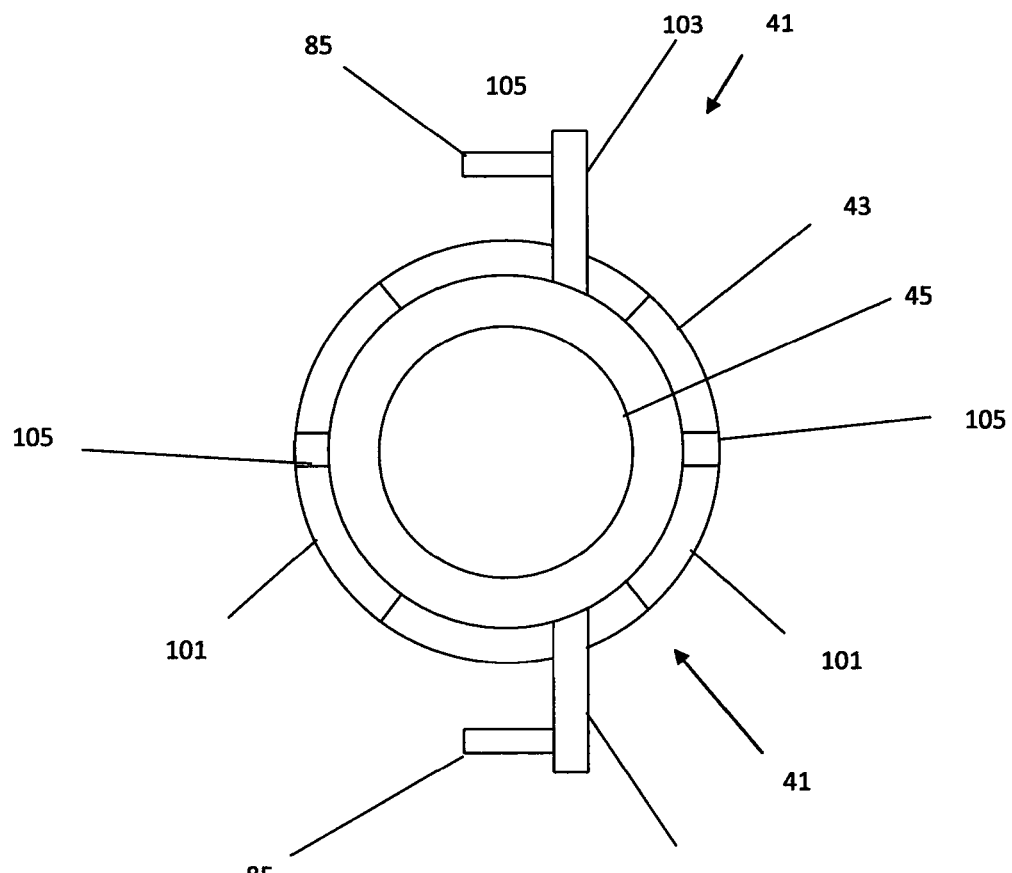
FIG. 3 is an end view of the syringe carrier, looking in a proximal direction.

The syringe carrier 5, shown in perspective view in FIG. 2 and in a distal end view in FIG. 3 (i.e. when viewed in the proximal direction), has a syringe flange cup 43, which is generally circular in cross-section. The cup 43 has an internal diameter that is slightly greater than the maximum dimension of the flange of a syringe 87 to be used with the auto-injector 1. The wall of the cup 43 is split into four sections. Two guide sections 101 and two arm sections 103. Each guide section 101 is provided with a slot 105. The cup 43 is also provided with a coaxially located syringe barrel orifice 45, which is of a diameter slightly greater than the external diameter of the syringe barrel 88. A cushioning element 47, in the form of an annular washer of elastomeric material is located at the bottom of the cup 43.

Figure 4:
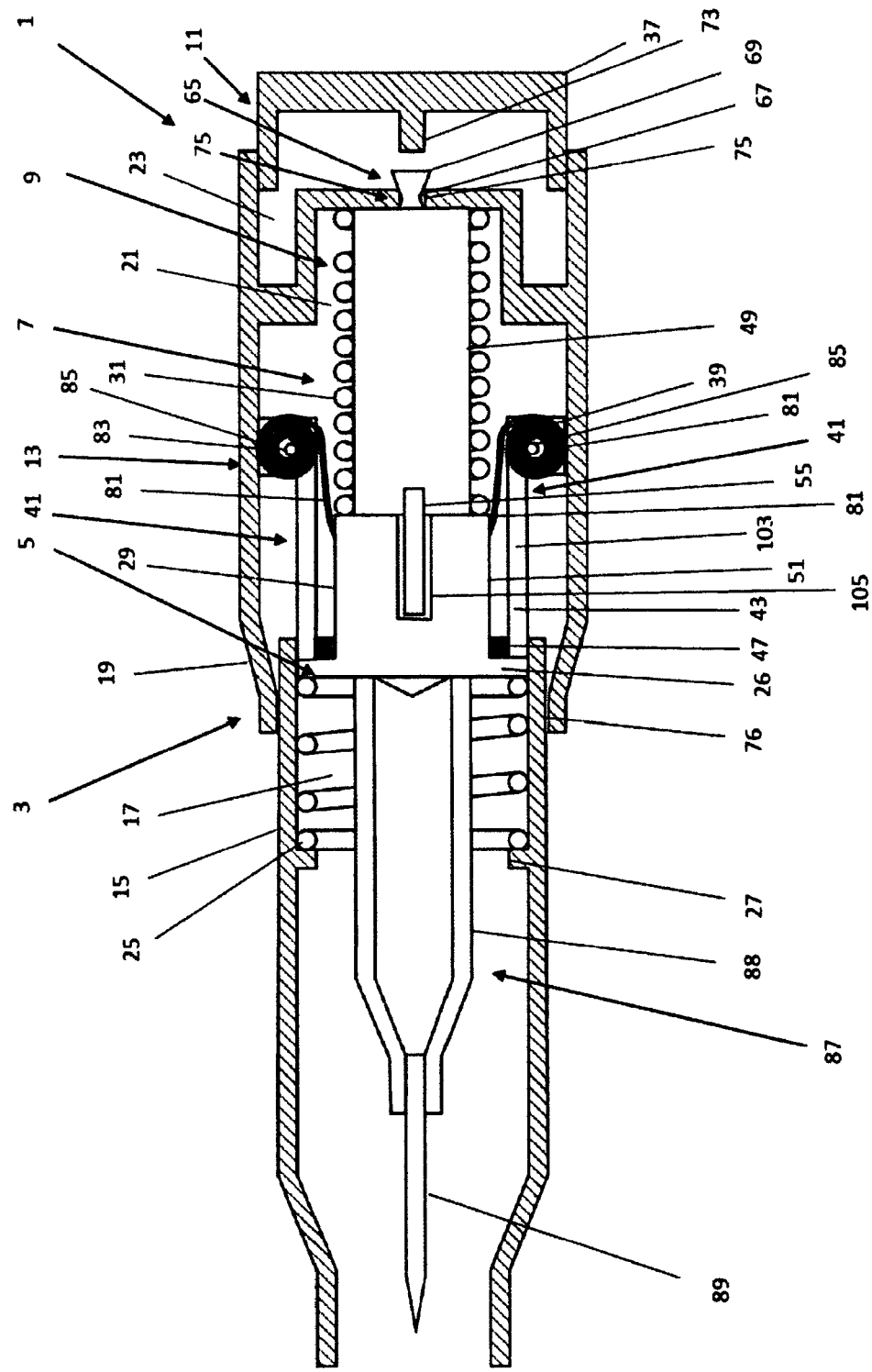
FIG. 4 is a view of the auto-injector of the first embodiment of the invention, in a primed and latched position, showing all the features of the auto-injector sectioned, with the exception of the syringe carrier and the syringe restraining member.

The syringe restraining member 29 of the needle insertion mechanism 7 is tubular and has a circular cross-section that varies in diameter along its length. The syringe restraining member 29 has a body 49 which is an elongate, straight-sided, tubular part with an annular external flange 51, which extends radially and perpendicularly outwardly from the body 49 at its proximal end. FIG. 4 illustrates the syringe restraining member 29 and the syringe carrier 5 in their complete, i.e. non-sectioned, states. The external flange 51 is provided with two diametrically opposed parallel sided spring slots 53 that pass from its proximal end face to its distal end face. The spring slots 53 have a sloped floor, with the transversely deepest part of the slot at the proximal end face of the flange 51. The external surface of the syringe restraining member 29 is also provided with two engagement tabs 55 which connect the syringe restraining member 29 with the syringe carrier 5 by engaging with slots 105 in the syringe carrier 5, in order to constrain relative axial and rotational movement of those two parts. The syringe restraining spring 31 is located around the outside of the main body of the syringe restraining member 29 and the annular flange 51 acts as a spring seat for one end of the spring 31.

The distal end of the body 49 is provided with an annular internal flange 57, which extends radially and perpendicularly inwardly from the body 49. The annular internal flange 57 extends only partially across the diameter of the body 49 and thus leaves a circular orifice 59. The annular flange 57 acts as a spring seat for one end of the plunger driving spring 35.

The plunger 33 is circular in cross-section and has a diameter that varies along its length. It is provided with a stem 61 having at its proximal end a driving head 63 and at its distal end a male latch part 65. The male latch part 65 has a waisted region 67, a head 69 and a transitional zone between those two parts. The diameters of the stem 61 and the male latch part 65 are less than the orifice 59 in the distal end of the syringe restraining member 29, such that they may pass through orifice 59. The waisted region 67 has a diameter that is smaller than the diameter of the head 69. The plunger 33 is located within the plunger driving spring 35 such that the spring locates around the stem 61. The driving head 63 acts as a spring seat for the proximal end of the plunger driving spring 35. The plunger 33 and the plunger driving spring 35 are located inside the syringe restraining member 29.

Interacting with the plunger 33 is an actuator 11. The actuator 11 comprises an actuation button 37 which is longitudinally slideable within an annular recess 23 provided in the drive mechanism housing 19. The actuation button 37 is cup-shaped with a circular cross-section. The open end of the button 37 engages with the recess 23, such that the button 37 can move in an axial direction but is restrained from moving in a radial direction. An actuation stud 73 is provided inside the button 37 on the proximally facing base of the button 37. The stud 73 is coaxially aligned with the female latch part 75 which is provided at the distal end of the drive mechanism housing 19.

The final part of the auto-injector 1 is the end of dose indication mechanism 13. The spirally coiled spring 39 of the end of dose indication mechanism 13 has a flat form, like a tape. An engagement section 79 located in the middle of the length of the spring 39 is formed with a flat profile that is complementary to the end face of the plunger 33. At either end of the engagement section 79 there is an arm 81 of the spring 39 which extends at an angle to the centerline of the auto-injector 1, and in a direction that is generally parallel to the base of the spring slots 55 in the annular flange 51. At the other end of each of the arms 81 there is provided a spirally coiled section 83. Each spirally coiled section 83 is retained on one of the strikers 41, by being wrapped around a peg 85.

During initial assembly of the auto-injector 1, for example by the manufacturer, the needle insertion mechanism 7 and the medicament delivery mechanism 9 are primed, ready for actuation by the end user, typically a patient who is self-administering a medicament contained within the syringe. Priming is achieved by pushing the plunger 33 towards the distal end of the auto-injector 1. This causes the plunger 33 to move into the syringe restraining member 29, against the force of the plunger driving spring 35, and it causes the syringe restraining member 29 to move into the spring chamber 21, against the force of the syringe restraining spring 31. After the syringe restraining member 29 has passed a certain distance into the spring chamber 21 the head 69 of the male latch part 65 of the plunger 33 comes into contact with the female latch part 75. The force applied to the female latch part 75 causes the two halves of the drive spring chamber 21 to move away from each other in a radial direction, thus opening up the orifice of the female latch part 75. The increase in the diameter of that orifice allows the male latch part 65 to pass through the end of the spring chamber 21, travelling in a proximal direction. Once the male latch part 65 has passed through the female latch part 75 the two halves of the drive spring chamber 21 can return to their original position, located around the waisted region 67 of the plunger 33, because the waisted region 67 has a diameter that is smaller than that of the female latch part 75. The plunger 33 is then latched in place.

During final assembly of the auto-injector 1, for example as carried out by the pharmaceutical company that manufactures the medicament, a syringe 87 which has a needle 89, an internal sliding bung 91 and a flange 75 is inserted into the syringe carrier 5.

Figure 5:
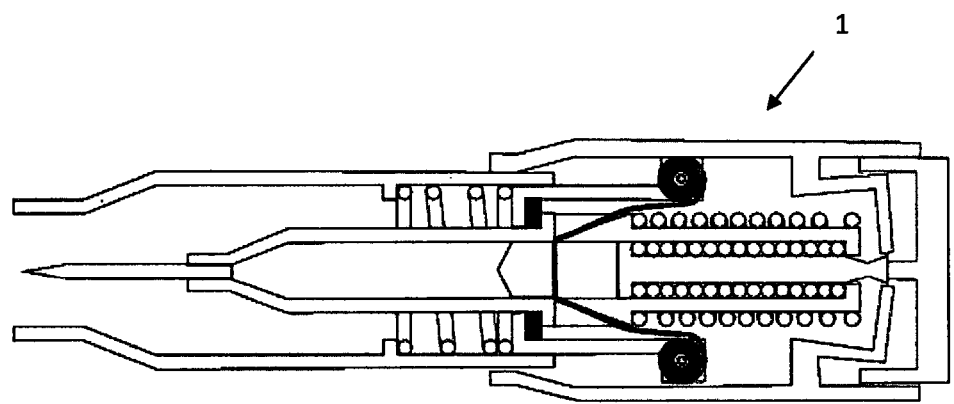
FIG. 5 is a cross-sectional view of the auto-injector of the first embodiment of the invention, immediately following actuation.
Figure 6:
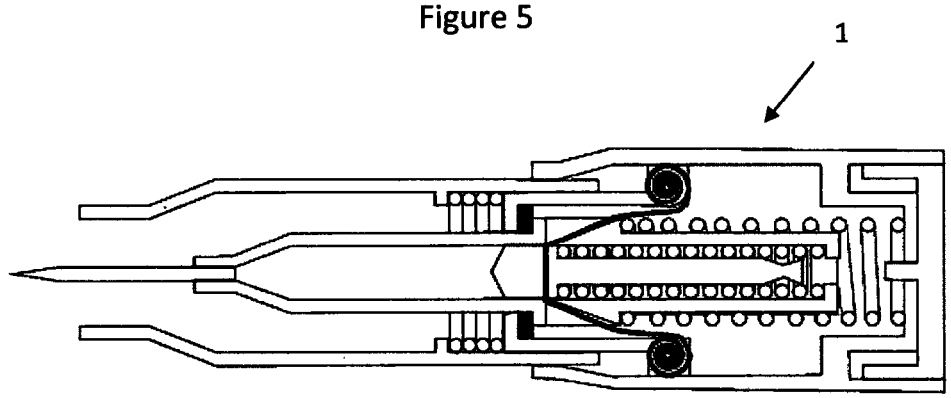
FIG. 6 is a cross-sectional view of the auto-injector of the first embodiment of the invention, during operation of the needle insertion mechanism.
Figure 7:
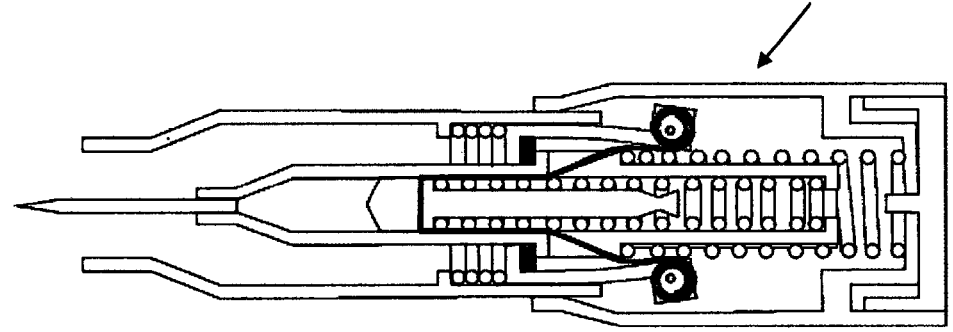
FIG. 7 is a cross-sectional view of the auto-injector of the first embodiment of the invention, during operation of the medicament delivery mechanism.
Figure 8:
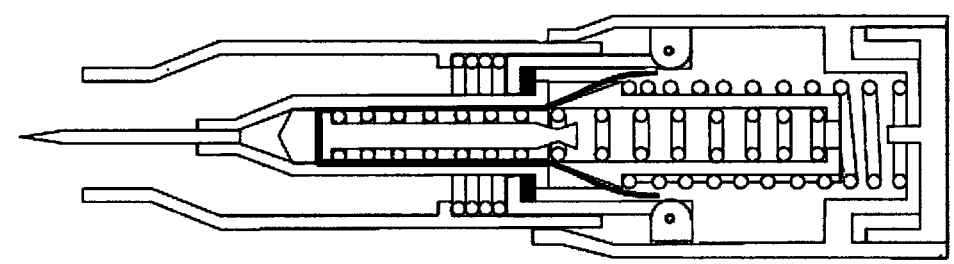
FIG. 8 is a cross-sectional view of the auto-injector of the first embodiment of the invention, immediately following an end of dose indication having been given to indicate completion of the medicament delivery phase.
Figure 9:
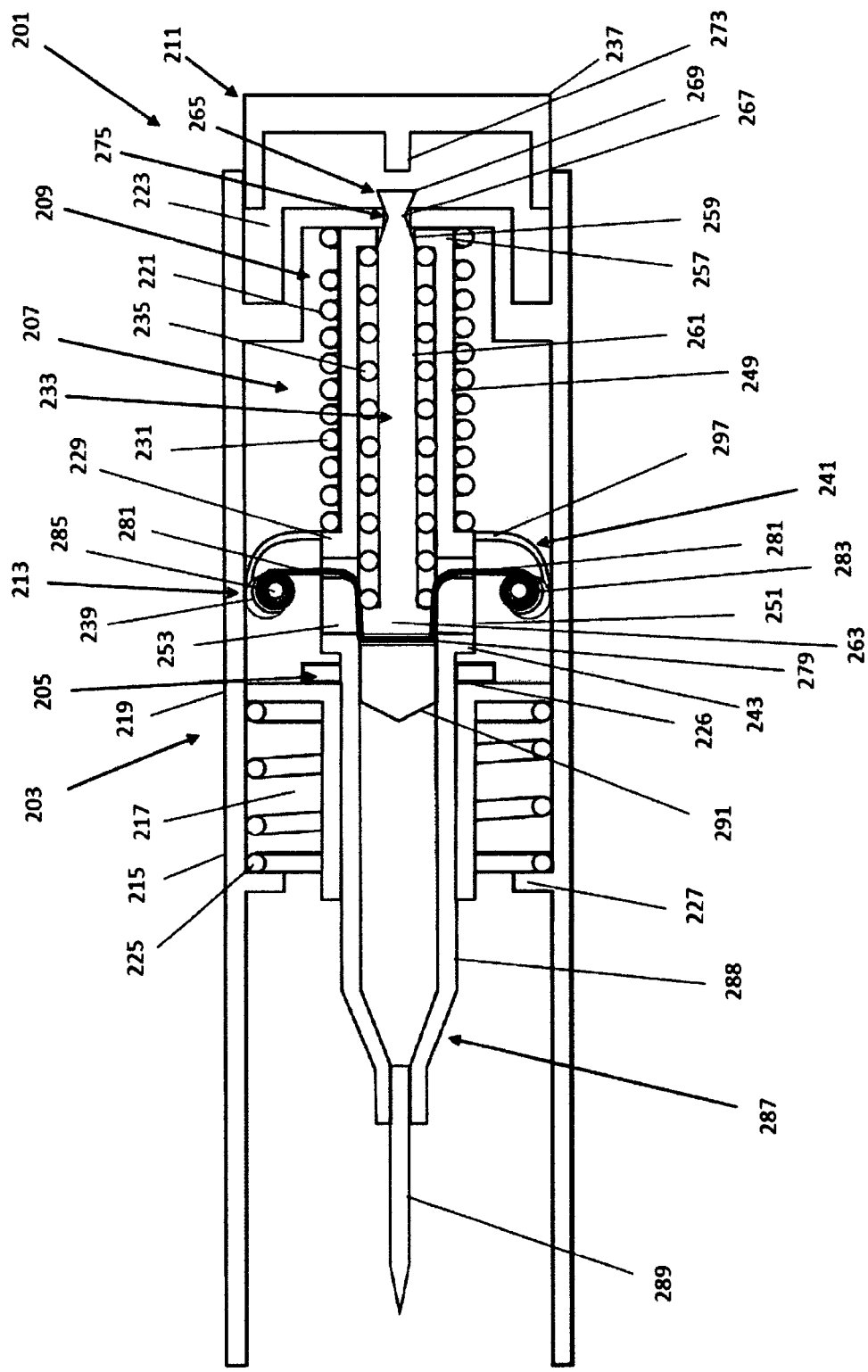
FIG. 9 is a cross-section view of an auto-injector according to a second embodiment of the invention, in a primed and latched position.

Operation of the auto-injector 1 takes place in five stages. First the user grips the auto-injector 1 in the palm of their hand such that they can press the button 37 with their thumb. The user then holds the proximal end of the syringe housing 15 against their skin, at the location where they wish the injection to take place. Commencement of injection occurs by pressing the actuation button 37 in a proximal direction, as shown in FIG. 5. Operation of the needle insertion mechanism 7 takes place next, as shown in FIG. 6, followed by operation of the medicament delivery mechanism 9, as shown in FIG. 7, and an end of dose indication, as shown in FIG. 8. Movement of the actuation button 37 in a proximal direction into the recess 23 in the drive mechanism housing 19 causes the actuation stud 73 to contact the distal end face of the male latch part 65 of the plunger 33. Further movement of the button 37 causes the male latch part 65 to be pushed through the circular orifice of the female latch part 75 thereby unlatching the needle insertion mechanism 7 and the medicament delivery mechanism 9 and allowing them to operate. Movement of the male latch part 65 through the female latch part 75 is assisted by the action of the plunger driving spring 35, which expands from a compressed state and pushes against the driving head 63. FIG. 5 illustrates the auto-injector 1 in this state. When the male latch part 65 has passed through the female latch part 75, the plunger driving spring 35 continues to act on the plunger 33 and the syringe restraining spring 31 continues to act on the syringe restraining member 29, moving both the plunger 33 and the syringe restraining member 29 towards the proximal end of the auto-injector 1 against the action of the syringe carrier bias spring 27. The syringe carrier 5 stops moving in a proximal direction when the syringe bias carrier spring 31 is fully compressed, i.e. the coils of the spring 27 are contacting each other. At this stage, the tip of the needle 89 of the syringe 87 has extended beyond the proximal end of the syringe housing 15 and has been inserted into the patient, at the desired injection site.

The next stage is delivery of the medicament, as shown in FIG. 7. Up until this point in the operation of the auto-injector 1 the bung 91 of the syringe 87 has not moved and thus no medicament has been administered to the patient, because the break out force that needs to be applied to the move the bung relative to the barrel of the syringe is greater than the force needed to compress the syringe carrier bias spring 27 and thus the syringe moves in a proximal direction before the bung does. With the syringe 87 fully deployed in the proximal direction the full force of the plunger driving spring 35, acting on the driving head 63 of the plunger 33, causes the plunger 33 to push against the bung 91, overcoming the breakout force. The bung 91 moves in a proximal direction and, forcing medicament out of the syringe 87, through the needle 89 and into the patient. Expansion of the plunger driving spring 35 will cause the bung 91 to be moved all the way along the syringe 87, until it reaches the bottom of the syringe 87 and stops.

At the same time as the plunger 33 is moving the bung 91, it is also acting on the spring 39 of the end of dose indication mechanism 13. The plunger's driving head 63 contacts the engagement section 79 of the spring 39 and moves it in the proximal direction. This increases the distance between the engagement section 79 and the spirally coiled sections 83 at the ends of the arms 81 and thus causes those spirally coiled sections 83 to gradually unwind by the same distance. FIG. 7 illustrates that stage of the operation. The spirally coiled sections 83 offer resistance to being unwound and as a result a force is applied to each of the strikers 41, via the pegs 85. The application of that force causes the strikers 41 to deflect in a direction towards the centre of the auto-injector 1 and away from the internal surface of the drive mechanism housing 19. The spirally coiled sections 83 continue to unwind until, at the point when the bung 91 reaches the end of the syringe 87 and can move no further, the coiled sections 83 are completely unwound and the arms 81 lose contact with the pegs 85. The strikers 41 are no longer restrained and they rebound in a direction towards the outside of the auto-injector 1 and impact the internal surface of the drive mechanism housing 19. That impact causes a noise and also imparts a vibration to the user, thus indicating the end of dose.

An auto-injector 201, according to a second embodiment of the present invention is shown in FIGS. 9 to 16. The auto-injector 201 has a different end of dose indication mechanism 213 to that provided in the auto-injector 1 of the first embodiment. In all other aspects, the construction and operation of the auto-injectors 1 and 201 are the same and features of the auto-injector 1 that are common to the auto-injector 201 are referenced with the same last two numerals, but prefixed with the number 2.

The end of dose indication mechanism 213 comprises a spirally coiled spring 239 which, when unwound as the result of the medicament delivery mechanism 209, causes the deflection and subsequent rebound of strikers 241 which are provided on the syringe restraining member 229 and which act upon the internal surface of the drive mechanism housing 219.

Figure 10:
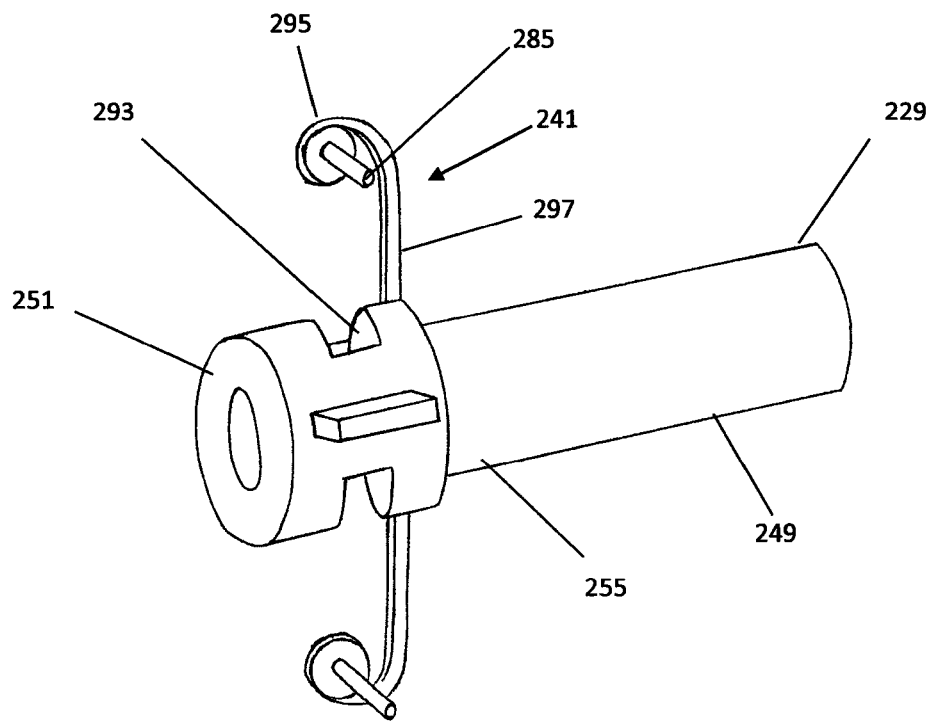
FIG. 10 is a perspective view of the syringe restraining member of the second embodiment.

The syringe restraining member 229 of the needle insertion mechanism 207, as illustrated in FIG. 10, is tubular and has a circular cross-section that varies in diameter along its length. The syringe restraining member 229 has a body 249 which is an elongate, straight-sided, tubular part with an annular external flange 251, which extends radially and perpendicularly outwardly from the body 249 at its proximal end. It is also provided with two engagement tabs 255, which serve the save purpose as the tabs 55 of the first embodiment. A radially extending hole or drilling passes through the external flange 251, perpendicularly to the longitudinal axis of the syringe restraining member 229 and with its axis passing through that longitudinal axis. The hole creates two slots 293 that link the internal bore of the syringe restraining member 229 with its external surface.

Figure 11:
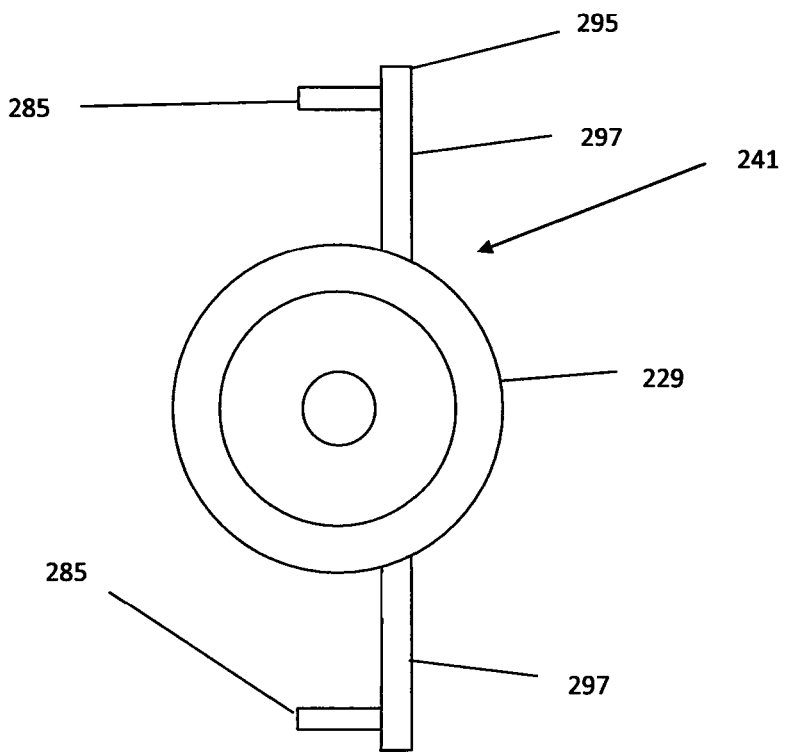
FIG. 11 is an end view of the syringe restraining member of the second embodiment.
Figure 12:
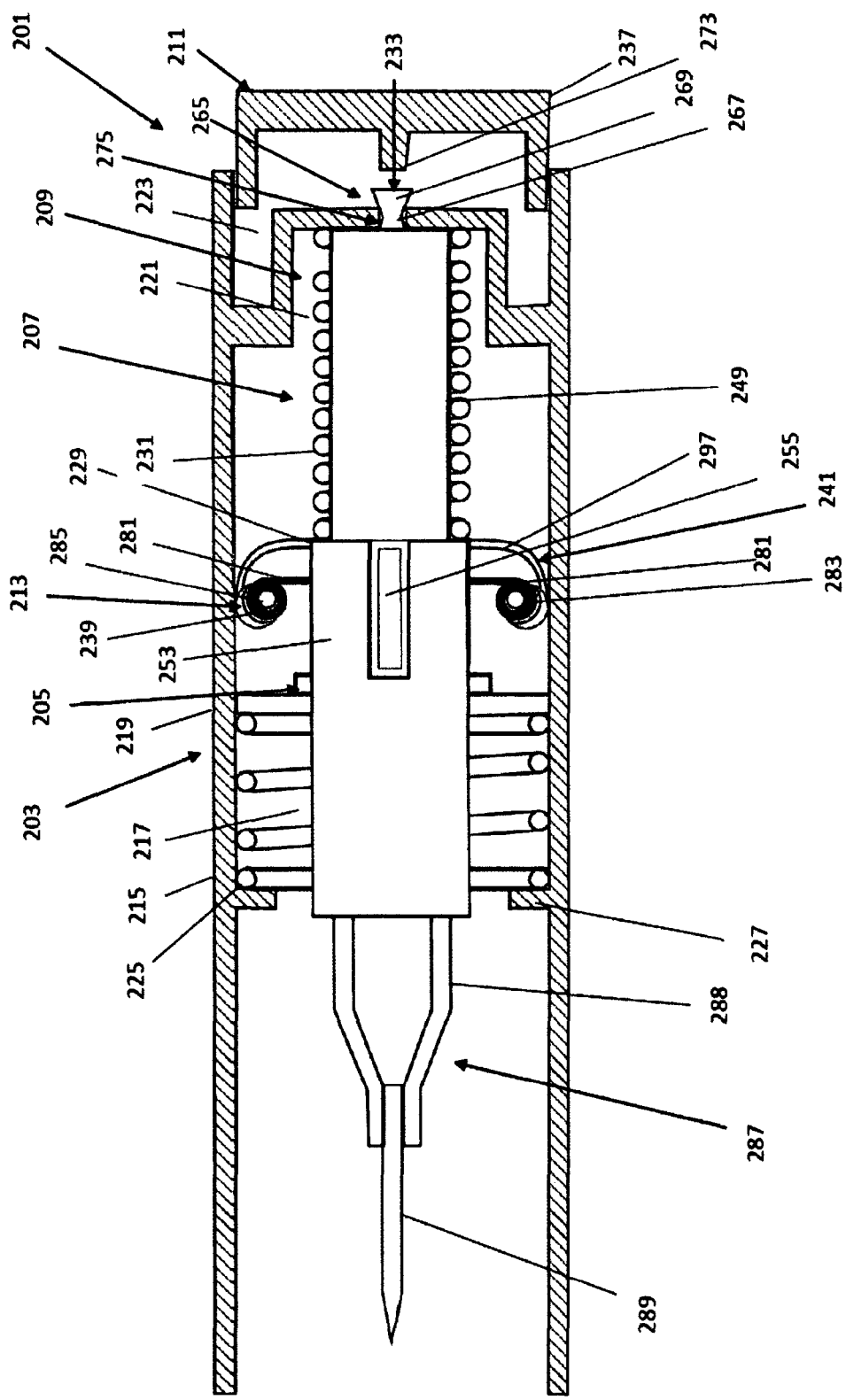
FIG. 12 is a view of the auto-injector of the second embodiment of the invention, in a primed and latched position, showing all the features of the auto-injector sectioned, with the exception of the syringe carrier and the syringe restraining member.
Figure 13:
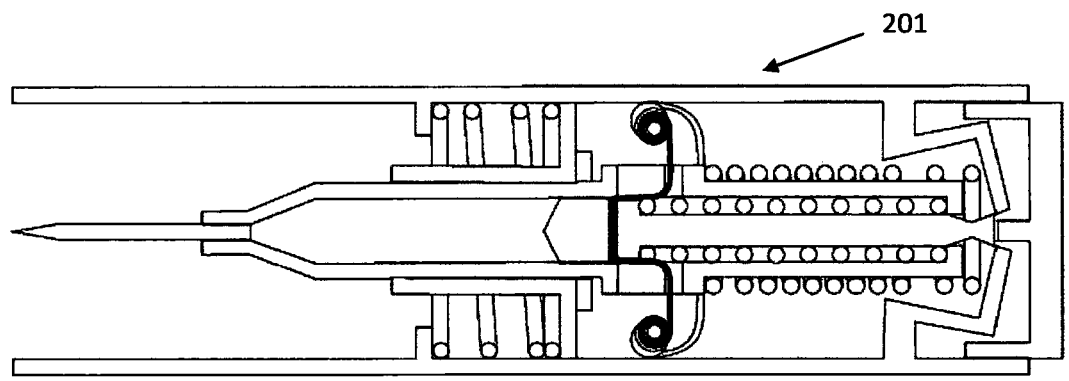
FIG. 13 is a cross-sectional view of the auto-injector of the second embodiment of the invention, immediately following actuation.
Figure 14:
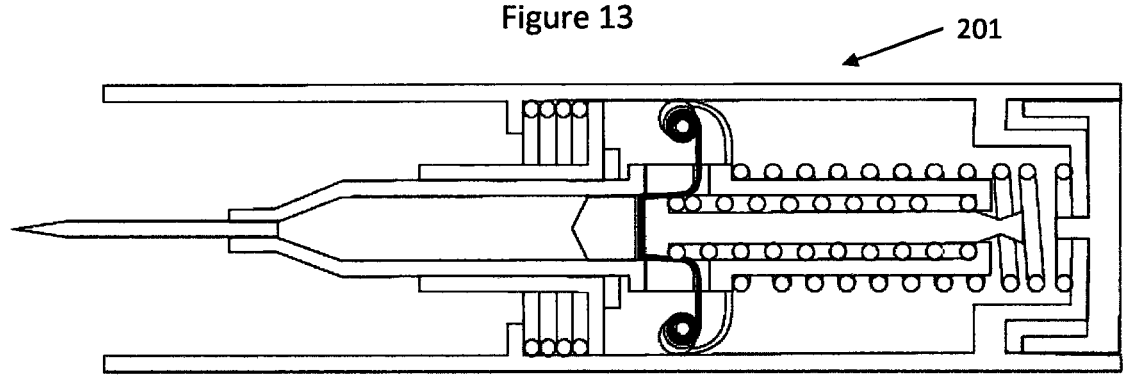
FIG. 14 is a cross-sectional view of the auto-injector of the second embodiment of the invention, during operation of the needle insertion mechanism.

Each striker 241 comprises a striking head 295 attached to one end of a resiliently deformable sprung stem 297. The other end of each sprung stem 297 is attached to the distal end of the flange 251 of the syringe restraining member 229 at a location that is offset from the longitudinal axis of the syringe restraining member 229. Each sprung stem 297 has a first straight section that extends perpendicularly from the surface of the syringe restraining member 229 and a second section that curves in a proximal direction between the first section and the striking head 295. Each striking head 295 is provided with a peg 285 which extends in a transverse direction and which is used to secure the spirally coiled spring 239. The sprung stems 297 are attached to the syringe restraining member 229 in a position that is offset from its centerline, so that the pegs 285 are located directly above the slots 293, as shown in FIG. 11. The sprung stems 297 bias the striking heads 295 against the internal wall of the drive mechanism housing 219.

The spring 239 has a flat form, like a tape. Located in the middle of the length of the spring 239 there is an engagement section 279. The engagement section 279 is located inside the body 249 of the syringe restraining member 229. At either end of the engagement section 279 the spring 239 continues with a spring arm 281. Each of the two spring arms 281 passes through a radially extending slot 293 in the body 249 and extends into the spring chamber 221 of the drive mechanism housing 219. The free end of each of the spring arms 281 forms a spirally coiled section 265 which is located around the peg 285 which is provided on each of the striking heads 295. That arrangement results in any slack in the spring 239 being taken up. The slots 293 and the striking heads 295 are located relative to each other such that the spring arms 281 extend in a substantially perpendicular direction, relative to the longitudinal axis of the auto-injector 1.

Operation of the auto-injector 201 is the same as for auto-injector 1, i.e. in the five stages that are (i) placing the auto-injector 201 adjacent to the injection site; (ii) pressing the actuation button 237; (iii) operation of the needle insertion mechanism 207; (iv) operation of the medicament delivery mechanism 209; and (v) completion of the dose, accompanied by an end of dose indication that may be audible and/or a vibration. Stages (ii) to (v) of which are illustrated in FIGS. 13 to 16.

Figure 15:
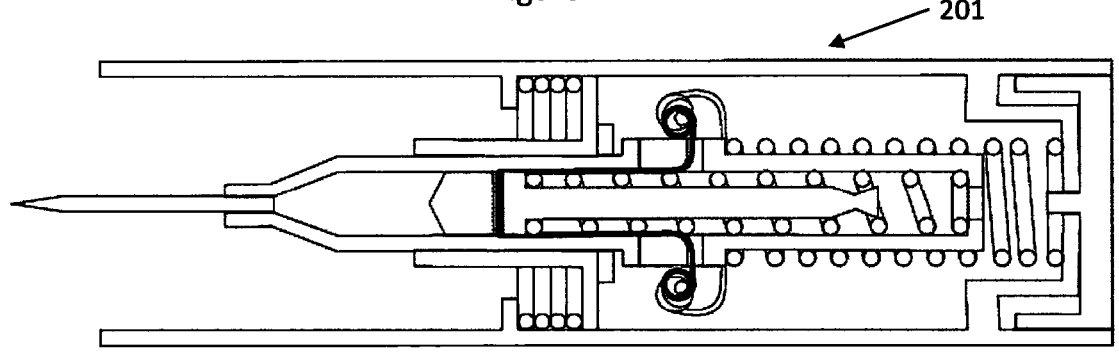
FIG. 15 is a cross-sectional view of the auto-injector of the second embodiment of the invention, during operation of the medicament delivery mechanism.
Figure 16:
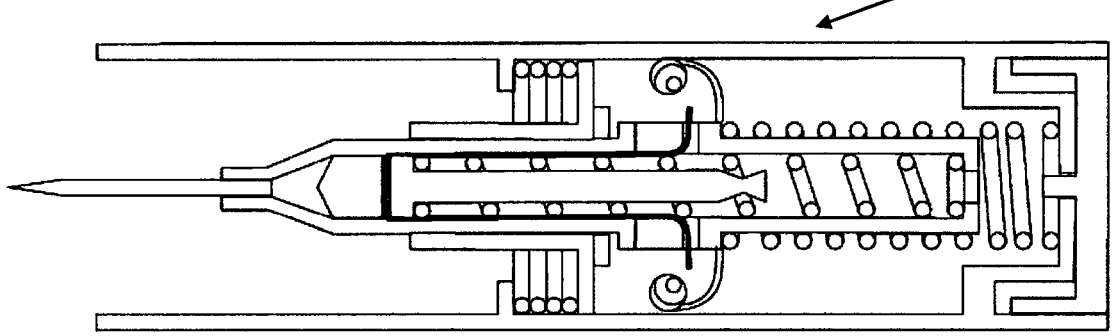
FIG. 16 is a cross-sectional view of the auto-injector of the second embodiment of the invention, immediately following an end of dose indication having been given to indicate the end of the medicament delivery phase.

Upon commencement of the medicament delivery stage, i.e. operation of the medicament delivery mechanism 209, the plunger 233 acts upon the bung 291 and pushes it in the proximal direction such that it moves relative to the barrel of the syringe 287. The plunger 233 also acts upon the engagement section 279 of the spring 239 and moves it in the proximal direction. This movement increases the distance between the engagement section 279 and the spirally coiled sections 265 and thus causes those spirally coiled sections 265 to gradually unwind such that the spring arms 281 pass through the slots 293. FIG. 15 illustrates that stage of the operation. The spirally coiled sections 265 offer resistance to being unwound and as a result a force is applied to each of the strikers 241, via the pegs 285, which causes the strikers 241 to deflect in a direction towards the centre of the auto-injector 201 and away from the internal surface of the drive mechanism housing 219. The spirally coiled sections 265 continue to unwind until, at the point when the bung 291 reaches the end of the syringe 287 and can move no further, the coiled sections 265 are completely unwound and the arms 281 lose contact with the pegs 85. The strikers 241 are then released and they rebound and impact the internal surface of the drive mechanism housing 219. That impact causes a noise and/or a vibration which is used to indicate the end of dose.

An auto-injector 301, according to a third embodiment of the present invention is shown in shown in FIGS. 17 to 25. The auto-injector 301 has a different end of dose indication mechanism 313 to that provided in the auto-injectors 1 and 201 of the first and second embodiments. In all other aspects, the construction and operation of the auto-injectors 201 and 301 are the same and the features of the auto-injector 301 that are common to the auto-injector 201 are referenced with the same last two numerals, but prefixed with the number 3.

The end of dose indication mechanism 313 comprises a spirally coiled spring 339 which, when unwound as a result of operation of the medicament delivery mechanism 309, causes the rotation of two striking wheels 341 which act upon striking plates 399 provided on the syringe restraining member 329.

The syringe restraining member 329 and the spring 339 have the same form as the corresponding components of the second embodiment.

Figure 17:
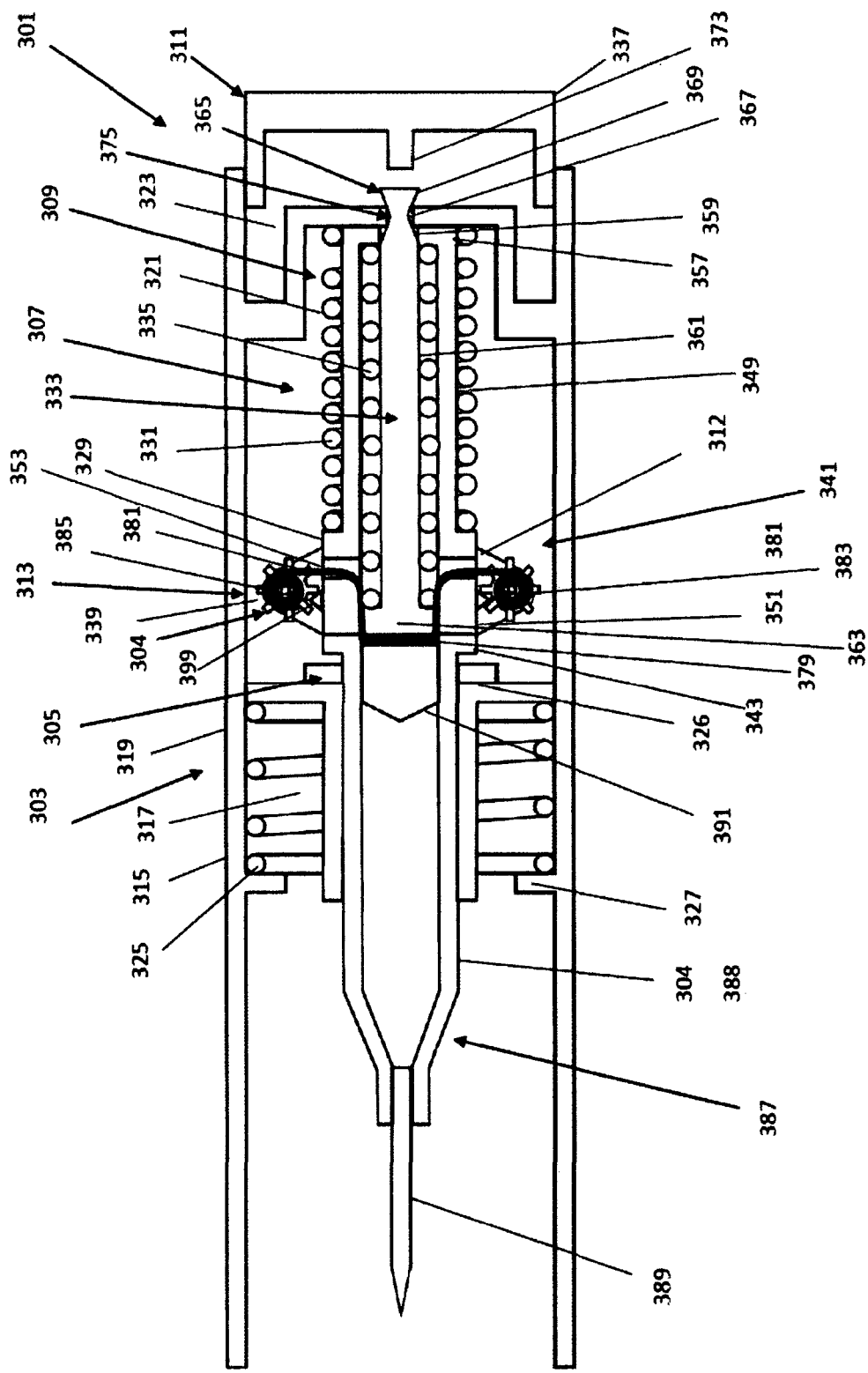
FIG. 17 is a cross-sectional view of an auto-injector according to a third embodiment of the invention, in a primed and latched position.
Figure 18:
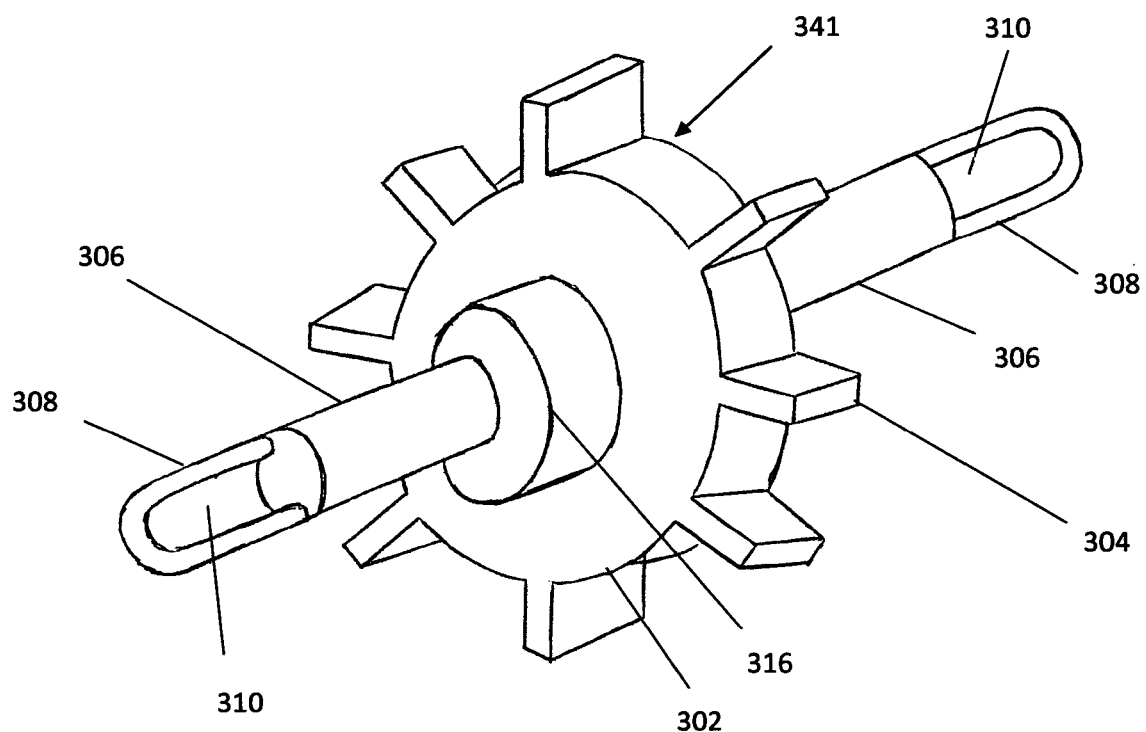
FIG. 18 is a perspective view of the syringe restraining member of the third embodiment.

This third embodiment has rotating striking wheels 341, as shown for example in FIGS. 17 and 18, rather than sprung arms. The striking wheels 341 are mounted on either side of the syringe restraining member 329. FIG. 18 shows a striking wheel 341 in perspective view. The striking wheel 341 is provided with a hub 302 around the external circumference of which are attached paddles 304. Stub axles 306 are fixed to either side of the hub 302 and are aligned coaxially with it. A U-shaped elastic element 308 is fitted to each stub axle 306. The free ends of the arms of the elastic element 308 are attached to the axially outer end of the stub axle 306 and those arms are aligned parallel with the longitudinal axis of the stub axle 306 such that a retaining loop 310 is created.

Figure 19:
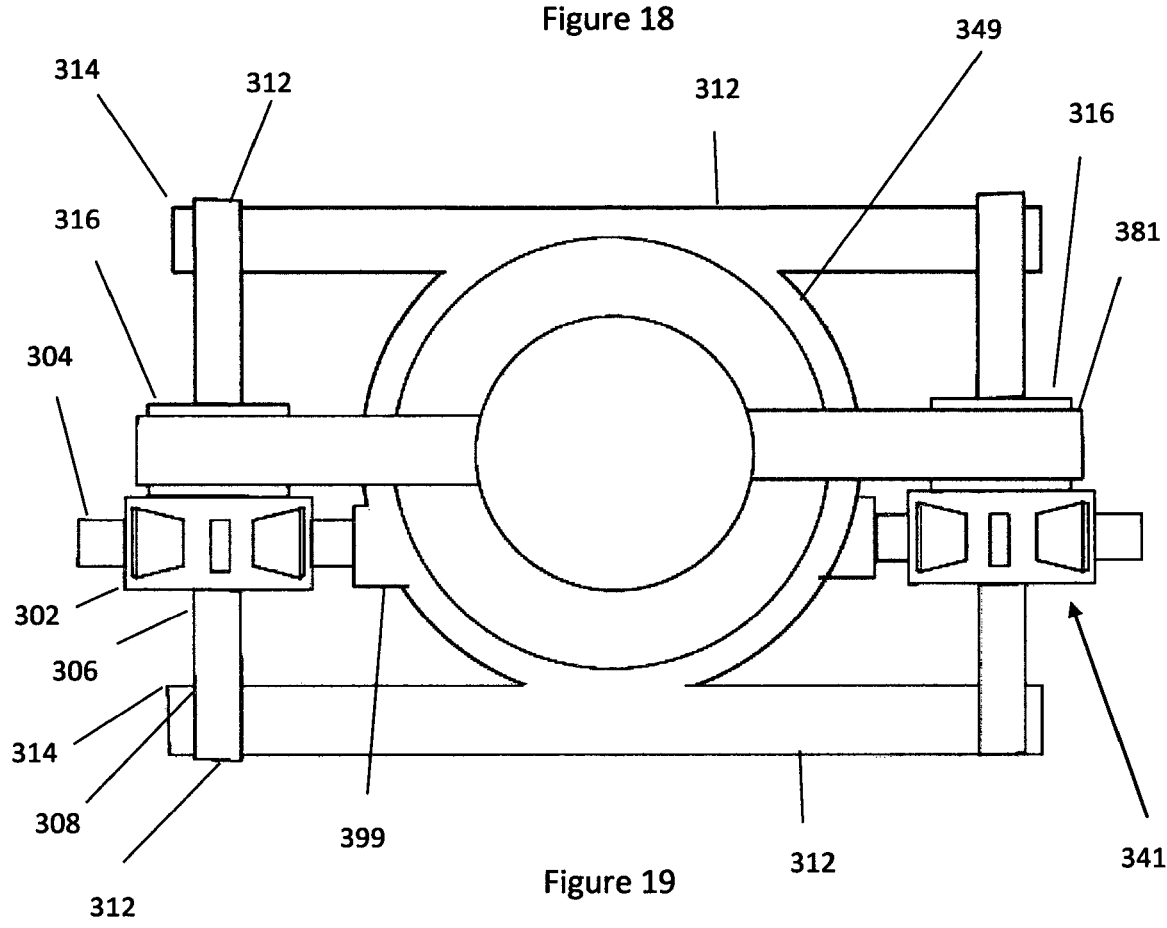
FIG. 19 is an end view of the syringe restraining member of the third embodiment.
Figure 20:
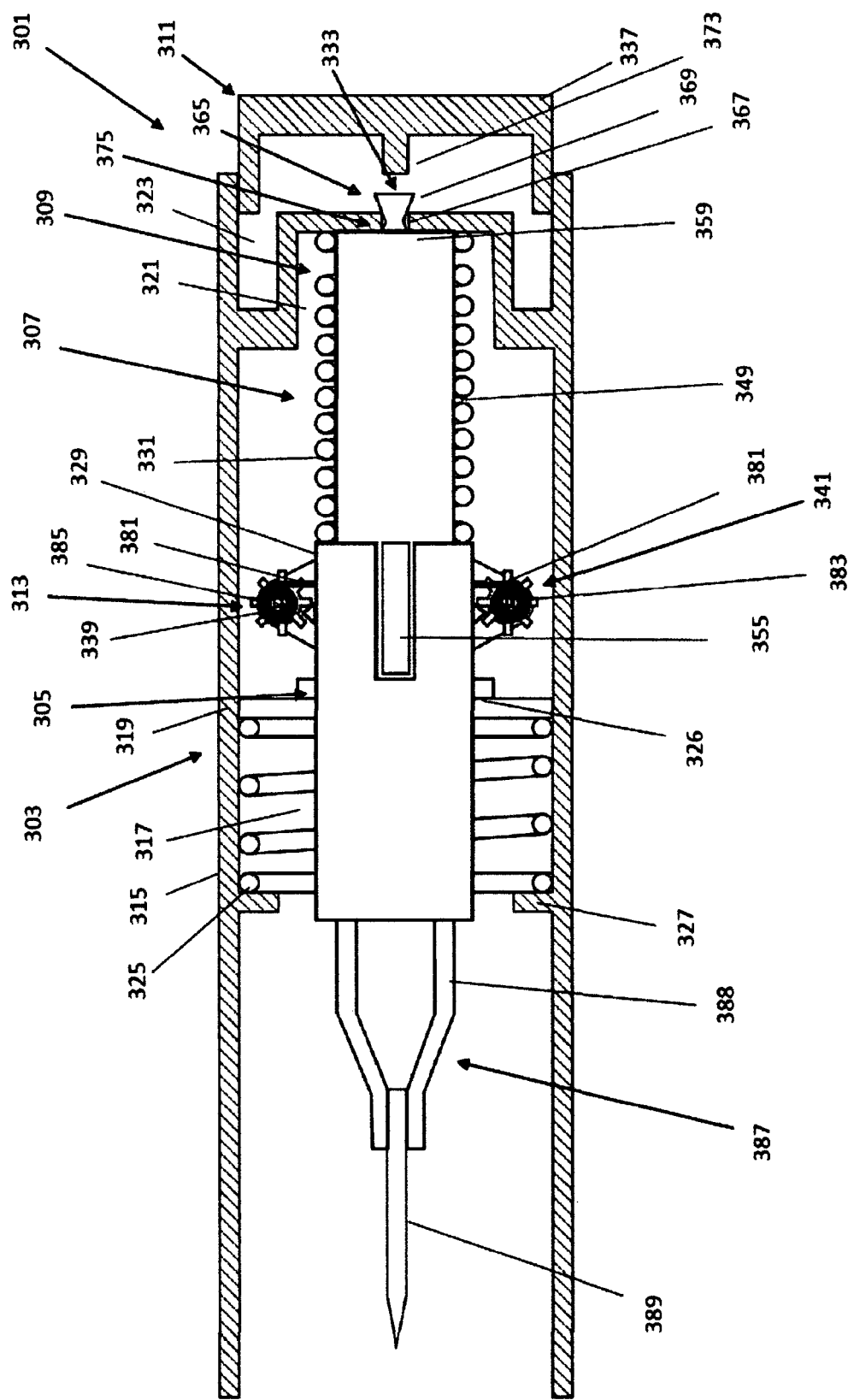
FIG. 20 is a view of the auto-injector of the third embodiment of the invention, in a primed and latched position, showing all the features of the auto-injector sectioned, with the exception of the syringe carrier and the syringe restraining member.
Figure 21:
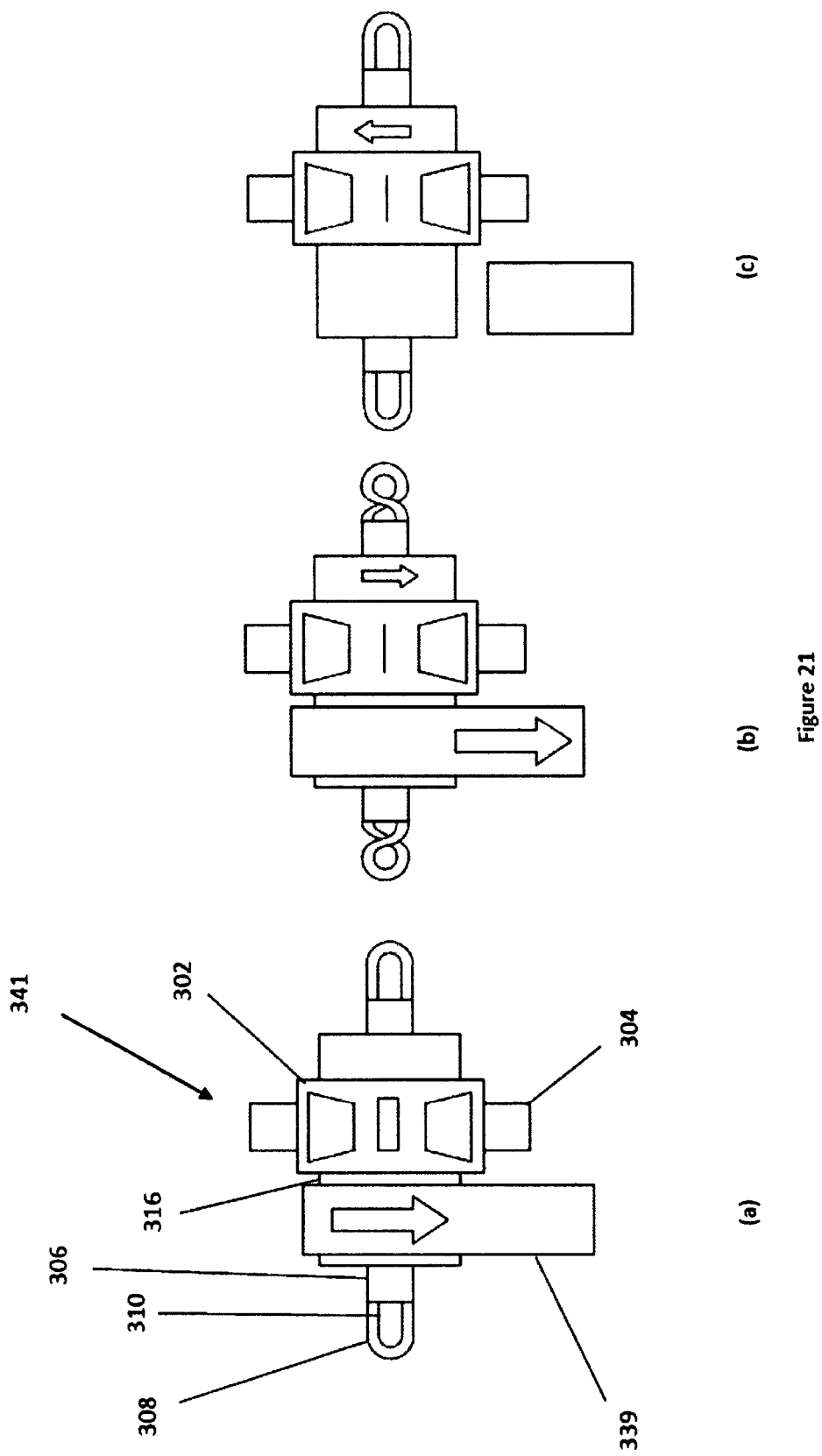
FIG. 21 is a view of the striker arrangement in three operational positions—(a) at commencement of the medicament delivery phase, (b) during the medicament delivery phase and (c) at the end of the medicament delivery phase.
Figure 22:
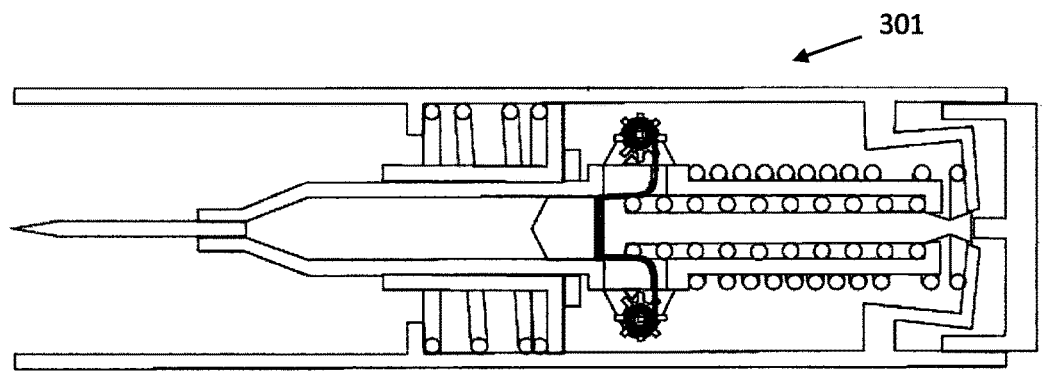
FIG. 22 is a cross-sectional view of the auto-injector of the third embodiment of the invention, immediately following actuation.
Figure 23:
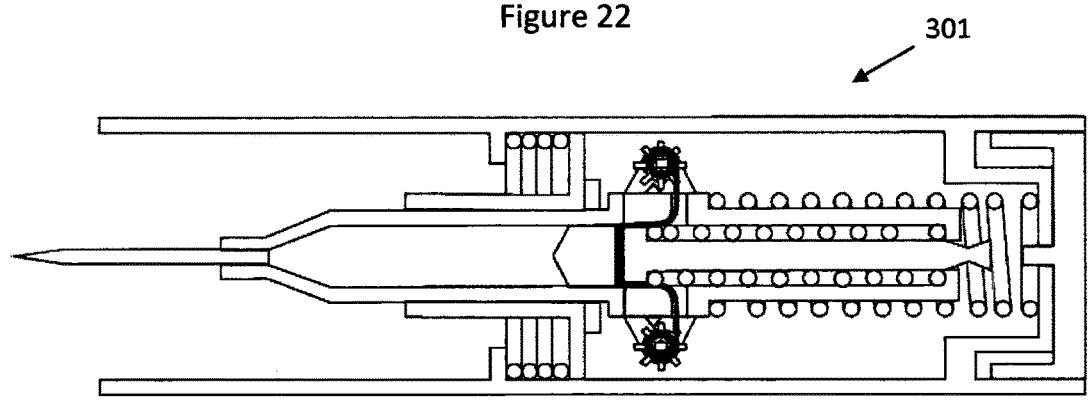
FIG. 23 is a cross-sectional view of the auto-injector of the third embodiment of the invention, during operation of the needle insertion mechanism.

The striking wheels 341 are mounted to the syringe restraining member 329, as illustrated in FIGS. 17 and 19, for example. Each striking wheel 341 is orientated transversally within the spring chamber 321 such that the longitudinal axes of its stub axles 306 run transversally and are offset from the longitudinal axis of the auto-injector 301 in a transverse direction. The striking wheel 341 is held in place by being attached to a pair of mounting brackets 312 which extend from the syringe pusher body 349. Each mounting bracket 312 is integral with the syringe pusher body and extends in a direction perpendicular to the longitudinal axes of the stub axles 306. The mounting brackets are provided with loop attachments 314. Each loop attachment 314 is configured to engage with a retaining loop 310 of the striking wheel 314 and hold the outer part of that retaining loop 310 such that it is constrained from rotating. The loop attachments 314 are spaced from the external circumference of the syringe pusher body 249 such that when the striking wheel 314 rotates, the paddles 304 contact one of the striking plates 399 but are able to pass across that striking plate 399 because of the flexibility of the paddles 304 and/or the striking plate 399.

A cylindrical drive pulley 316 is formed integrally and coaxially with the hub 302 on one side of each of the striking wheel 341. Each spring arm 381 of the spring 339 is spirally wound around one of the drive pulleys 316 (in the primed or semi-deployed positions of the plunger 339). The drive pulleys 316 are aligned with the spring arms 381, which are aligned with the longitudinal axis of the auto-injector 301 and pass through that axis. Consequently, the paddles 304 and the striking plates 399 are offset from the centerline of the auto-injector 301. The slots 393 in the syringe restraining member 329 are located relative to the striking wheels 341 such that the spring arms 381 extend between the drive pulleys 316 and the inside surface of the syringe pusher body 349 in a substantially straight line, perpendicular to the longitudinal axis of the injector.

Operation of the auto-injector 301 is the same as for the auto-injectors 1 and 201, i.e. in the five stages that are (i) placing the auto-injector 301 adjacent to the injection site; (ii) pressing the actuation button 337; (iii) operation of the needle insertion mechanism 307; (iv) operation of the medicament delivery mechanism 309; and (v) completion of the dose, accompanied by an end of dose indication. Stages (ii) to (v) of which are illustrated in FIGS. 21 to 25.

Figure 24:
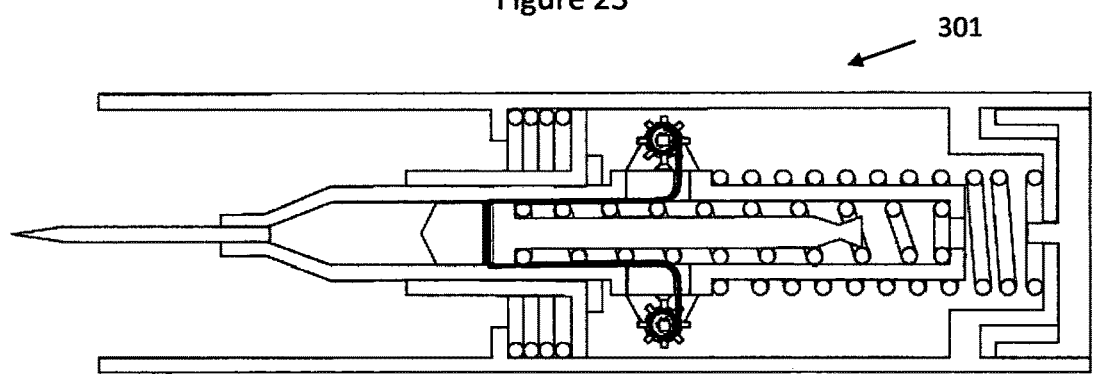
FIG. 24 is a cross-sectional view of the auto-injector of the third embodiment of the invention, during operation of the medicament delivery mechanism.
Figure 25:
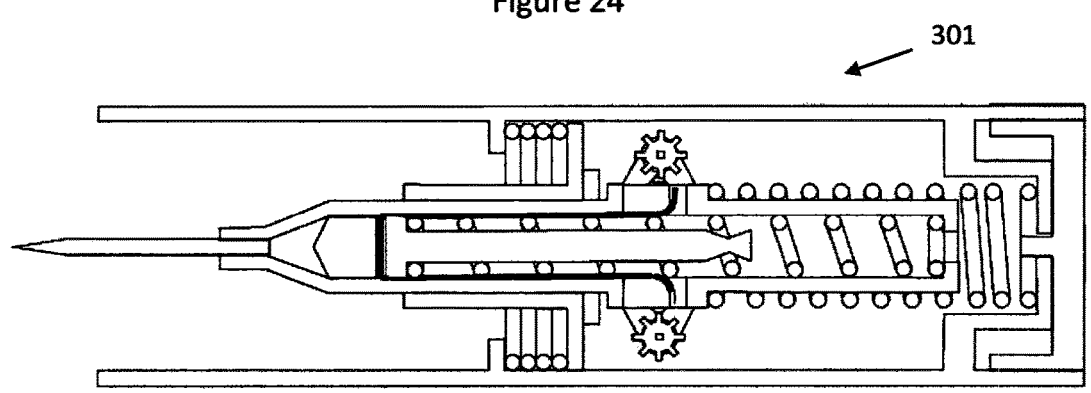
FIG. 25 is a cross-sectional view of the auto-injector of the third embodiment of the invention, immediately following an end of dose indication having been given to indicate the end of the medicament delivery phase.

Upon commencement of the medicament delivery stage, i.e. operation of the medicament delivery mechanism 309, the plunger 333 acts upon the bung 391 and pushes it in the proximal direction such that it moves relative to the barrel of the syringe 387. The plunger 333 also acts upon the flat section 379 of the spring 339 and moves it in the proximal direction. This movement increases the distance between the flat section 379 and the spirally coiled sections 365 and thus causes those spirally coiled sections 365 to gradually unwind and for the spring arms 381 to pass through the slots 393. FIG. 24 illustrates that stage of the operation. The spirally coiled sections 365 offer resistance to being unwound and as a result a force is applied to each of the striking wheels 341, via the drive pulleys 316, which causes the striking wheels 341 to rotate. As the striking wheels 341 rotate the paddles 304 come into contact with the striking plates 399 and make an audible noise and/or a vibration. Rotation of the striking wheels 341 causes the elastic elements 308 to twist, because they are held at their outer ends by the loop attachments 314 on the mounting plates 312. The spirally coiled sections 365 continue to unwind until, at the point when the bung 391 reaches the end of the syringe 387 and can move no further, the coiled sections 365 are completely unwound and the arms 381 lose contact with the drive pulleys 316. At this point the striking wheels 341 counter rotate, driven by the untwisting of the elastic elements 308. The paddles 304 again contact the striking plates 399, but this time in quick succession, resulting in a rapid audible clicking noise and/or an accompanying vibration which signals the end of dose.

Figure 26:
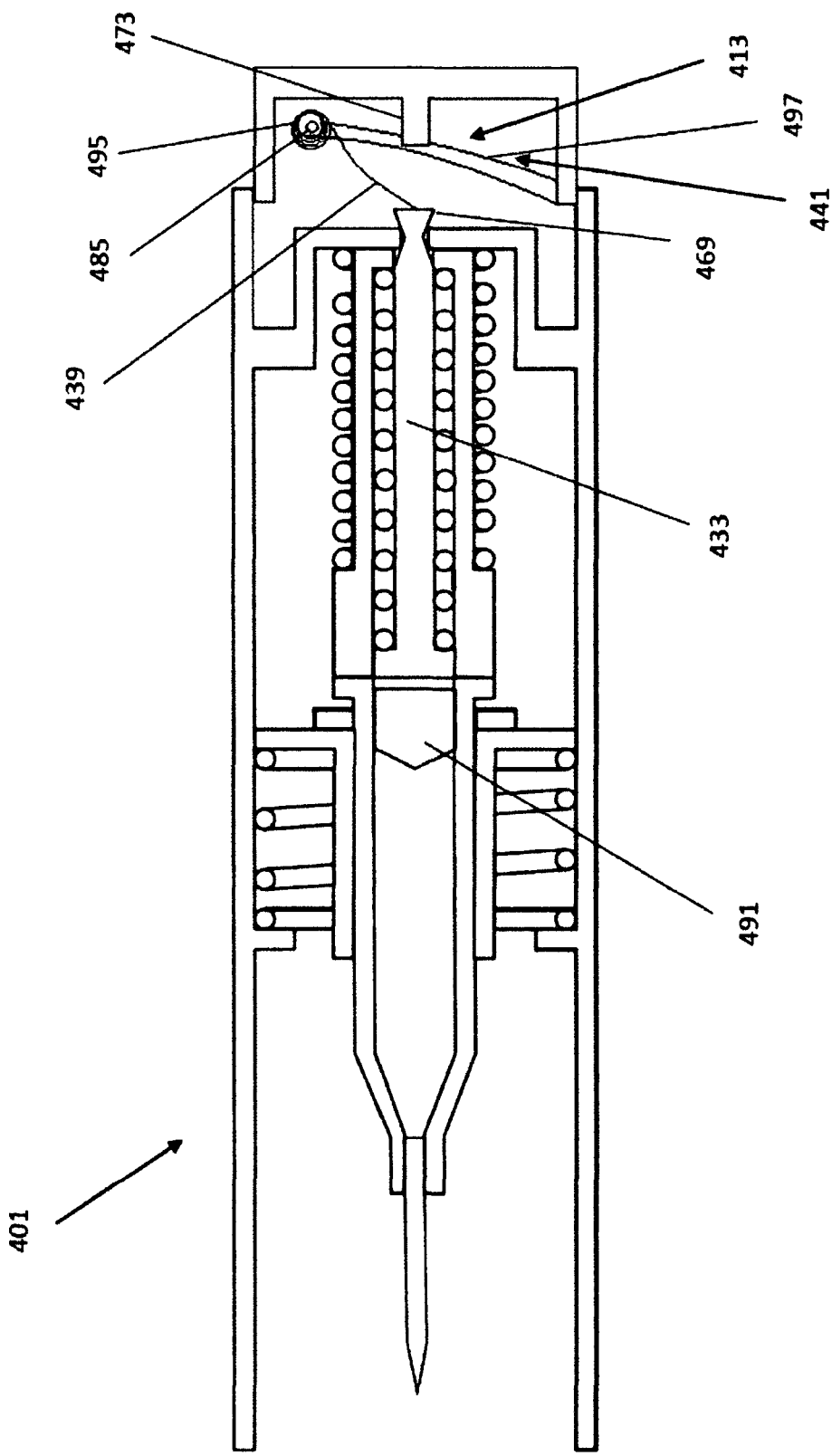
FIG. 26 is a cross-section view of an auto-injector according to a fourth embodiment of the invention, in a primed and latched position.

An auto-injector 401, according to a fourth embodiment of the present invention is shown in FIG. 26. The auto-injector has a different end of dose indication mechanism 413 to that provided in the auto-injectors 1, 201 and 301 of the first, second and third embodiments. In all other aspects, the construction and operation of the auto-injectors 201, 301 and 401 are the same and the features of the auto-injector 401 that are common to the auto-injectors 201 and 301 are referenced with the same last two numerals, but prefixed with 4.

The end of dose indication mechanism 413 comprises a spirally coiled spring 439 which is unwound as a result of the movement of the plunger 433 in a proximal direction during operation of the medicament delivery mechanism 409. The increase in the tension in the spring 439 when it is unwound causes the deflection and subsequent rebound of a striker 441 which is attached to the side wall of the actuation button 437 and which acts upon the internal surface of the actuation button 437.

The striker 441 comprises a resiliently deformable sprung stem 497 to one end of which is attached a striking head 495. The other end of the sprung stem 497 is attached to a side wall of the actuation button 437. The sprung stem 497 is offset from the longitudinal axis of the auto-injector 401 so that it can pass the actuation stud 473. The striking head 495 is provided with a peg 485 which extends in a transverse direction and which is used to hold the coiled end of spirally coiled spring 439. The other end of the spirally coiled spring 439 is attached to the head 469 of the plunger 433.

Operation of the auto-injector 401 is the same as for the auto-injectors 1, 201 and 301, i.e. in the five stages that are (i) placing the auto-injector 401 adjacent to the injection site; (ii) pressing the actuation button 437; (iii) operation of the needle insertion mechanism 407; (iv) operation of the medicament delivery mechanism 409; and (v) completion of the dose, accompanied by an end of dose indication.

Upon commencement of the medicament delivery stage, the plunger 433 moves in a proximal direction, the spring 439 is placed under tension and it begins to unwind. The resistance that the spring 439 presents to its unwinding results in a force being applied to the peg 485, such that the resiliently deformable sprung arm 497 of the striker 441 deflects in a proximal direction. The spirally coiled section of the spring 439 continues to unwind as the plunger 433 moves in a proximal direction until, at the point when the plunger 433 has pushed the bung 491 to the end of the syringe 487 such that it can move no further, the spring 439 has been unwound entirely and it loses contact with the peg 485. The striker 441 is no longer constrained at its moving end and the rebound of the sprung arm 497 drives the striking head 495 in a distal direction until it strikes the inside surface of the actuation button 437. That strike produces a noise and/or a vibration which is used to indicate the end of dose to the user.

Figure 27:
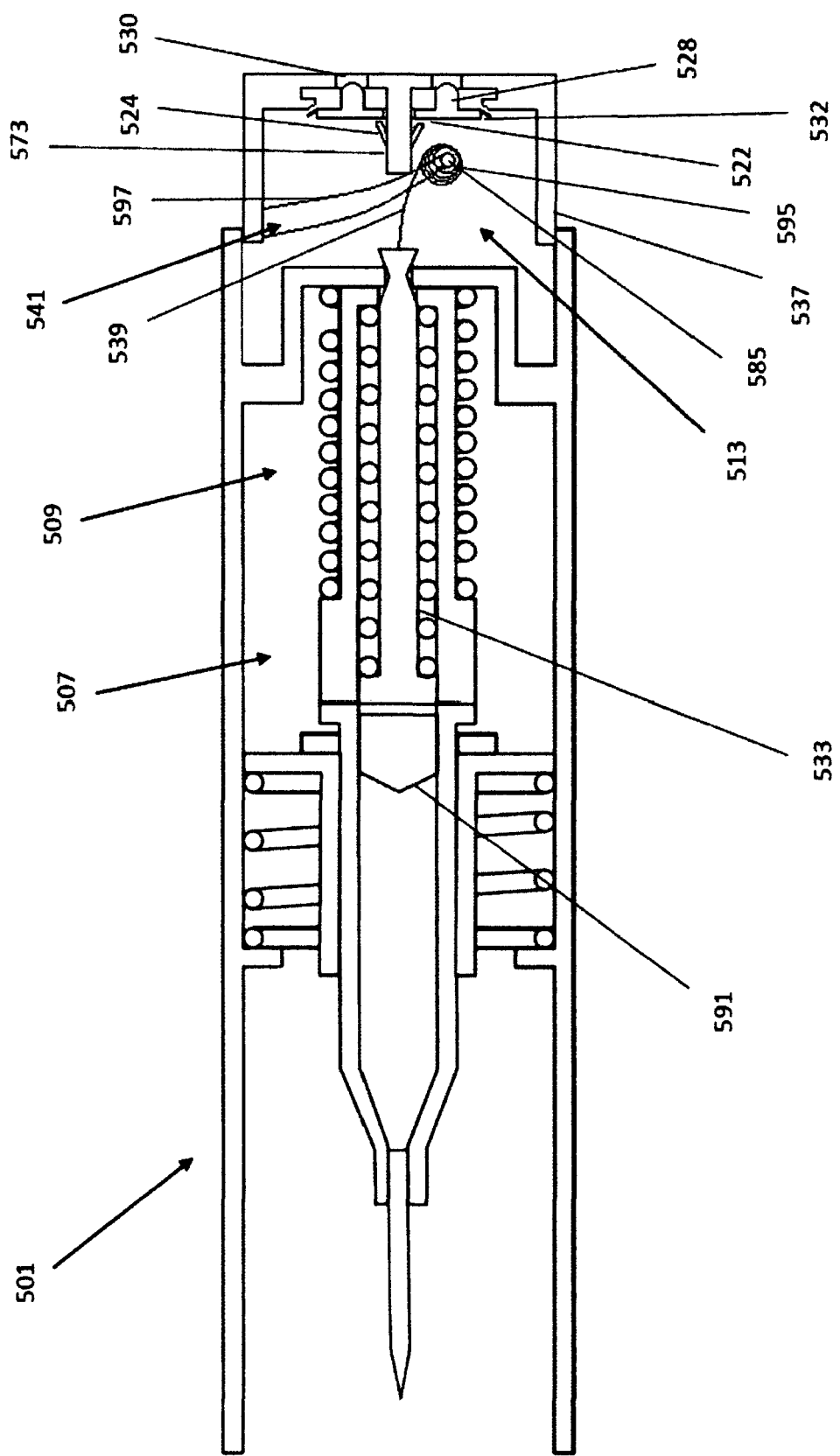
FIG. 27 is a cross-section view of an auto-injector according to a fifth embodiment of the invention, in a primed and latched position.

An auto-injector 501, according to a fifth embodiment of the present invention is shown in FIG. 27. The auto-injector has a similar end of dose indication mechanism 513 to that provided in the auto-injector 401 of the fourth embodiment but with the addition of a visual and tactile end of dose indication. In all other aspects, the construction and operation of the auto-injectors 401 and 501 are the same and the features of the auto-injector 501 that are common to the auto-injector 401 are referenced with the same last two numerals, but prefixed with 5.

The end of dose indication mechanism 513 additionally comprises an annular indicator washer 522 that is transversely oriented and coaxially located within the drive mechanism housing 519. The indicator washer 522 is slideably movable in a longitudinal direction, guided by the actuation stud 573 which passes through the orifice in the centre of the indicator washer 522. Movement of the indicator washer 522 in a proximal direction is constrained by a flange 524 provided on the actuation stud 573, over which the indicator washer 522 cannot pass when travelling in a proximal direction. The annular indicator washer 522 is provided with two tactile protrusions 528 which extend longitudinally from the indicator washer in a distal direction. The tactile protrusions 528 are aligned with holes 530 provided in the actuation button 537 and are sized so that they can protrude through those holes 530. Latch arms 532 are provided on the inside of the actuation button 537 for engagement with the indicator washer 522.

Operation of the auto-injector 501 is the same as for the auto-injectors 1, 201, 301 and 401, i.e. in the five stages that are (i) placing the auto-injector 501 adjacent to the injection site; (ii) pressing the actuation button 537; (iii) operation of the needle insertion mechanism 507; (iv) operation of the medicament delivery mechanism 509; and (v) completion of the dose, accompanied by an end of dose indication.

Upon commencement of the medicament delivery stage, the plunger 533 moves in a proximal direction, the spring 539 is placed under tension and it begins to unwind. The resistance that the spring 539 presents to its unwinding results in a force being applied to the peg 585, such that the resiliently deformable sprung arm 597 of the striker 541 deflects in a proximal direction. The spirally coiled section of the spring 539 continues to unwind as the plunger 533 moves in a proximal direction until, at the point when the plunger 533 has pushed the bung 591 to the end of the syringe 587 such that it can move no further, the spring 539 has been unwound entirely and it loses contact with the peg 585. The striker 541 is no longer constrained at its moving end and the rebound of the sprung arm 597 drives the striking head 595 in a distal direction until it strikes the indicator washer 522. The force of the impact between the striking head 595 and the indicator washer 522 drives the indicator washer 522 in a distal direction and causes the distal face of the indicator washer 522 to come into abutment with the proximal face of the actuation button 537. At that position, the latch arms 532 engage with the proximal face of the indicator washer 522 and hold the indicator washer 522 in a latched position. In that latched position the tactile protrusions 528 pass through the holes 530 in the actuation button 537 and protrude above the external surface of the actuation button 537 such that the user feels the protrusions 528 against their thumb and is thus provided with a tactile feedback signal. In addition, the abutment of the indicator washer 522 with the actuation button 537 creates an audible noise and/or a vibration to indicate the end of dose to the user.

The invention claimed is:

1. A medicament delivery device comprising:
a container for a medicament;
a plunger for acting upon the medicament within the container to expel the medicament from the container;
a plunger drive mechanism;
a plunger drive energy source;
a connector;
a dose indicator; and
a dose indication energy storage mechanism that is resiliently deformable for storing energy and which is connected to the plunger by the connector at an end of the dose indication energy storage mechanism by a releasable attachment, the dose indication energy storage mechanism also being coupled to the dose indicator, and wherein:
the medicament delivery device is configured such that, during its operation, movement of the plunger under action of the plunger drive mechanism causes energy from the plunger drive energy source to be imparted to the dose indication energy storage mechanism by resiliently deforming the dose indication energy storage mechanism and to be stored by the dose indication energy storage mechanism and wherein upon the plunger reaching substantially an end of its travel, the releasable attachment between the connector and the dose indication energy storage mechanism is released and the dose indication energy storage mechanism acts upon the dose indicator, the dose indicator interacting with the medicament delivery device to produce an end of dose indication.

2. A medicament delivery device according to claim 1, wherein the connector comprises a connection element and a retractor configured to retract the connection element to an un-extended position, wherein the retractor keeps the connection element in tension during a medicament delivery phase of the operation of the medicament delivery device.

3. A medicament delivery device according to claim 1, wherein the connector comprises a tape and at least part of the tape is a spirally wound spring.

4. A medicament delivery device according to claim 1, wherein at least a part of the dose indication energy storage mechanism is resiliently deformable and is deformed during a medicament delivery phase of the operation of the medicament delivery device.

5. A medicament delivery device according to claim 1, wherein the releasable attachment comprises a peg attached to a striker part of the dose indication storage energy mechanism.

6. A medicament delivery device claim 1, wherein the dose indication energy storage mechanism comprises at least one resiliently deformable arm which is fixedly attached to another part of the medicament delivery device at a fixed end and which has a free end which is free to move, wherein the free end is provided with a striker part, the connector being attached to the at least one resiliently deformable arm, at least initially, wherein, during one phase of the operation of the medicament delivery device, movement of the plunger causes the at least one resiliently deformable arm to deflect and during another phase of the operation of the medicament delivery device, the connector becomes detached from the at least one resiliently deformable arm and the at least one resiliently deformable arm rebounds and strikes a part of the medicament delivery device, in order to produce the end of dose indication.

7. A medicament delivery device according to claim 6, wherein the dose indication energy storage mechanism comprises two resiliently deformable arms each provided with a striker head, wherein the striking heads are configured to strike the inside of a housing part of the medicament delivery device.

8. A medicament delivery device according to claim 1, wherein the dose indication energy storage mechanism comprises at least one resiliently deformable element which is fixedly attached to another part of the medicament delivery device at a fixed end and at its other end is fixedly attached to a striker carrier carrying at least one striker, the connector being attached to the striker carrier, at least initially, wherein, during one phase of operation of the medicament delivery device, movement of the plunger causes the striker carrier to rotate in a first direction and during another phase of the operation of the medicament delivery device, the connector becomes detached from the striker carrier and the striker carrier rotates in a second direction, driven by a rebounding of the at least one resiliently deformable element, wherein the at least one striker strikes a part of the medicament delivery device, in order to produce the end of dose indication.

9. A medicament delivery device according to claim 8, wherein rotation of the striker carrier in the first direction causes the at least one striker to strike a part of the medicament delivery device, in order to produce an indication that a dose is being delivered whilst the plunger is moving.

10. A medicament delivery device according to claim 1, wherein the dose indication energy storage mechanism comprises at least one resiliently deformable arm which is fixedly attached to another part of the medicament delivery device at a fixed end and which has a free end which is free to move, wherein the free end is provided with a striker part, the connector being attached to the at least one resiliently deformable arm, at least initially, wherein, during one phase of operation of the medicament delivery device, movement of the plunger causes the at least one resiliently deformable arm to deflect and during another phase of operation of the medicament delivery device, the connector becomes detached from the at least one resiliently deformable arm and the at least one resiliently deformable arm rebounds and strikes a firing button, in order to produce an end of dose indication.

11. A medicament delivery device according to claim 1, wherein the dose indication energy storage mechanism comprises at least one resiliently deformable arm which is fixedly attached to another part of the medicament delivery device at a fixed end and which has a free end which is free to move, wherein the free end is provided with a striker part, the connector being attached to the at least one resiliently deformable arm, at least initially, wherein the medicament delivery device further comprises a moveable indicator and a housing part, or a firing button, that enables at least a part of the moveable indicator to become raised above an external surface of the medicament delivery device and wherein, during one phase of operation of the medicament delivery device, movement of the plunger causes the at least one resiliently deformable arm to deflect and during another phase of operation of the medicament delivery device, the connector becomes detached from the at least one resiliently deformable arm and the at least one resiliently deformable arm rebounds and strikes the moveable indicator and moves the moveable indicator relative to the housing part or firing button such that at least a part of the moveable indicator is at least momentarily raised above the external surface of the medicament delivery device.

12. A medicament delivery device according to claim 1, wherein the medicament delivery device comprises:
an initial position in which the dose indication energy storage mechanism is in a first position;
an energized position in which the dose indication energy storage mechanism is resiliently deformed and stores energy in response to the movement of the plunger; and
an end position in which the dose indication energy storage mechanism is in a second position, wherein, when in the second position, the energy stored in the energized position has been released and the dose indication energy storage mechanism is not resiliently deformed.

13. A medicament delivery device according to claim 12, wherein the first position of the dose indication energy storage mechanism and the second position of the dose indication energy storage mechanism are the same.

* * * * *